United States Patent
Lafferty et al.

(10) Patent No.: US 7,291,460 B2
(45) Date of Patent: Nov. 6, 2007

(54) MULTIPLEXED SYSTEMS FOR NUCLEIC ACID SEQUENCING

(75) Inventors: Mike Lafferty, Encinitas, CA (US); Charles Tweedy, San Diego, CA (US); James Butler, San Diego, CA (US)

(73) Assignee: Verenium Corporation, San Diego, CA (US)

( * ) Notice: Subject to any disclaimer, the term of this patent is extended or adjusted under 35 U.S.C. 154(b) by 618 days.

(21) Appl. No.: 10/452,157

(22) Filed: May 30, 2003

(65) Prior Publication Data

US 2003/0224439 A1    Dec. 4, 2003

Related U.S. Application Data

(60) Provisional application No. 60/384,880, filed on May 31, 2002.

(51) Int. Cl.
   *C12Q 1/68* (2006.01)
(52) U.S. Cl. ......................................................... 435/6
(58) Field of Classification Search ..................... None
   See application file for complete search history.

(56) References Cited

U.S. PATENT DOCUMENTS

| | | | |
|---|---|---|---|
| 4,355,153 A | 10/1982 | Radici et al. | |
| 4,415,732 A | 11/1983 | Caruthers et al. | |
| 4,458,066 A | 7/1984 | Caruthers et al. | |
| 4,652,613 A | 3/1987 | Collins et al. | |
| 4,683,195 A | 7/1987 | Mullis et al. | |
| 4,683,202 A | 7/1987 | Mullis | |
| 4,725,677 A | 2/1988 | Koster et al. | |
| 4,800,159 A | 1/1989 | Mullis et al. | |
| 4,965,188 A | 10/1990 | Mullis et al. | |
| 4,973,679 A | 11/1990 | Caruthers et al. | |
| 4,980,460 A | 12/1990 | Molko et al. | |
| 5,068,269 A | 11/1991 | Diamantoglou | |
| 5,302,509 A | 4/1994 | Cheeseman | |
| 5,552,278 A | 9/1996 | Brenner | |
| 5,578,832 A | 11/1996 | Trulson et al. | |
| 5,599,675 A | 2/1997 | Brenner | |
| 5,599,695 A | 2/1997 | Pease et al. | |
| 5,632,957 A | 5/1997 | Heller et al. | |
| 5,698,089 A | 12/1997 | Lewis et al. | |
| 5,710,000 A | 1/1998 | Sapolsky et al. | |
| 5,714,330 A | 2/1998 | Brenner | |
| 5,795,557 A | 8/1998 | Pajonk et al. | |
| 5,831,065 A | 11/1998 | Brenner | |
| 5,843,767 A | 12/1998 | Beattie | |
| 5,858,671 A * | 1/1999 | Jones ............................ | 435/6 |
| 5,939,261 A | 8/1999 | Loewy et al. | |
| 5,981,956 A | 11/1999 | Stern | |
| 5,990,479 A | 11/1999 | Weiss et al. | |
| 6,013,445 A | 1/2000 | Albrecht et al. | |
| 6,024,872 A | 2/2000 | Mahendran et al. | |
| 6,025,601 A | 2/2000 | Trulson et al. | |
| 6,027,894 A | 2/2000 | Sapolsky et al. | |
| 6,045,996 A | 4/2000 | Cronin et al. | |
| 6,048,457 A | 4/2000 | Kopaciewicz et al. | |
| 6,066,448 A | 5/2000 | Wohlstadter et al. | |
| 6,083,763 A | 7/2000 | Balch | |
| 6,096,817 A | 8/2000 | Mc Namara | |
| 6,150,147 A | 11/2000 | Goldberg et al. | |
| 6,197,498 B1 | 3/2001 | Koster | |
| 6,197,503 B1 | 3/2001 | Vo-Dinh et al. | |
| 6,207,229 B1 | 3/2001 | Bawendi et al. | |
| 6,207,392 B1 | 3/2001 | Weiss et al. | |
| 6,225,077 B1 | 5/2001 | Schmidt et al. | |
| 6,251,600 B1 | 6/2001 | Winger et al. | |
| 6,258,533 B1 | 7/2001 | Jones | |
| 6,268,222 B1 | 7/2001 | Chandler et al. | |
| 6,291,181 B1 | 9/2001 | Sapolsky et al. | |
| 2002/0080350 A1 | 6/2002 | Lafferty | |

FOREIGN PATENT DOCUMENTS

| | | |
|---|---|---|
| EP | 0703991 B1 | 5/2001 |
| EP | 0927267 B1 | 4/2002 |
| WO | WO9106678 A1 | 5/1991 |
| WO | WO9321340 A1 | 10/1993 |
| WO | WO9612039 A1 | 4/1996 |
| WO | WO9810095 A1 | 3/1998 |
| WO | WO9815652 A1 | 4/1998 |
| WO | WO9848047 A2 | 10/1998 |
| WO | WO9937814 A1 | 7/1999 |
| WO | WO0113120 A1 | 2/2001 |

OTHER PUBLICATIONS

Chan et al (Science (1998) 281:2016-2018).*
Allawi and Santalucia, Thermodynamics and NMR of internal G.T mismatches in DNA. Biochemistry. Aug. 26, 1997;36(34):10581-94.
Alves and Carr, Dot blot detection of point mutations with adjacently hybridising synthetic oligonucleotide probes. Nucleic Acids Res. Sep. 12, 1988;16(17):8723.
Beaucage and Iyer, Advances in the Synthesis of Oligonucleotides by the Phosphoramidite Approach, Tetrahedron, Mar. 1992, 48(12):2223-2311.
Bommarito, et al., Thermodynamic parameters for DNA sequences with dangling ends. Nucleic Acids Res. May 1, 2000;28(9):1929-34.
Brenner et al., In vitro cloning of complex mixtures of DNA on microbeads: physical separation of differentially expressed cDNAs. Proc Natl Acad Sci U S A. Feb. 15, 2000;97(4):1665-70.
Canard and Sarfati, DNA polymerase fluorescent substrates with reversible 3'-tags. Gene. Oct. 11, 1994;148(1):1-6.
Ferris et al., N-cyanomidazole and diimidazole imine: water-soluble condensing agents for the formation of the phophodiester bond, Nucleosides & Nucleotides, 1989, 8: 407-414.

(Continued)

*Primary Examiner*—Jeffrey Fredman
(74) *Attorney, Agent, or Firm*—Kalim Fuzail (57) ABSTRACT

Methods for the sequencing of polynucleotides are provided. Also provided are multiplex systems for sequencing polynucleotides using the disclosed methods, kits for use with the disclosed methods and methods for diagnosing diseases and adverse drug reactions using the disclosed methods.

2 Claims, 2 Drawing Sheets

OTHER PUBLICATIONS

Guatelli, et al., Isothermal, in vitro amplification of nucleic acids by a multienzyme reaction modeled after retroviral replication. Proc Natl Acad Sci U S A. Mar. 1990;87(5):1874-8.

Han and Rutter, Lambda gt22S, a phage expression vector for the directional cloning of cDNA by the use of a single restriction enzyme SfiI. Nucleic Acids Res. Dec. 23, 1988;16(24)11837.

Han, et al., Quantitative profiling of differentiation-induced microsomal proteins using isotope-coded affinity tags and mass spectrometry. Nat Biotechnol. Oct. 2001;19(10):946-51.

Hunkapiller, et al., Large-scale and automated DNA sequence determination. Science. Oct. 4, 1991;254(5028):59-67.

Kwoh, et al., Transcription-based amplification system and detection of amplified human immunodeficiency virus type 1 with a bead-based sandwich hybridization format. Proc Natl Acad Sci U S A. Feb. 1989;86(4):1173-7.

Landegren, et al., A ligase-mediated gene detection technique. Science. Aug. 26, 1988;241(4869):1077-80.

Maxam and Gilbert, A new method for sequencing DNA. Proc Natl Acad Sci U S A. Feb. 1977;74(2)560-4.

Metzker, et al., Termination of DNA synthesis by novel 3'-modified-deoxyribonucleoside 5'-triphosphates. Nucleic Acids Res. Oct. 11, 1994;22(20):4259-67.

Nelson, et al., Effect of site-specific methylation on restriction endonucleases and DNA modification methyltransferases. Nucleic Acids Res. Jul. 1, 1993;21(13):3139-54.

Nicewarner-Pena, et al., Submicrometer metallic barcodes. Science. Oct. 5, 2001;294(5540):137-41.

Padgett and Sorge, Creating seamless junctions independent of restriction sites in PCR cloning. Gene. Feb. 2, 1996;168(1):31-5.

Pirmohamed and Park, Genetic susceptibility to adverse drug reactions, Trends Pharmacol Sci., Jun. 2001,22(6):298-305.

Polyak and Riggins, Gene discovery using the serial analysis of gene expression technique: implications for cancer research, J Clin Oncol, Jun. 1, 2001, 19(11):2948-58.

Roberts, et al., REBASE: restriction enzymes and methyltransferases. Nucleic Acids Res. Jan. 1, 2003;31(1):418-20.

Samiotaki, et al., Dual-color detection of DNA sequence variants by ligase-mediated analysis. Genomics. Mar. 15, 1994;20(2):238-42.

Sanger, et al., DNA sequencing with chain-terminating inhibitors. Proc Natl Acad Sci U S A. Dec. 1977;74(12):5463-7.

Santalucia, A unified view of polymer, dumbbell, and oligonucleotide DNA nearest-neighbor thermodynamics. Proc Natl Acad Sci U S A. Feb. 17, 1998;95(4):1460-5.

Shabarova, et al., Chemical ligation of DNA: the first non-enzymatic assembly of a biologically active gene. Nucleic Acids Res. Aug. 11, 1991;19(15):4247-51.

Somers, et al., A rapid, reliable method for detection of known point mutations: point-EXACCT. Nucleic Acids Res. Nov. 11, 1994, 22(22):4840-1.

Wu and Wallace, Specificity of the nick-closing activity of bacteriophage T4 DNA ligase. Gene. 1989;76(2):245-54.

Wu and Wallace, The ligation amplification reaction (LAR)—amplification of specific DNA sequences using sequential rounds of template-dependent ligation. Genomics. May 1989;4(4):560-9.

* cited by examiner

Figure 2

MULTIPLEXED SYSTEMS FOR NUCLEIC ACID SEQUENCING

CROSS REFERENCE TO RELATED APPLICATIONS

This application claims the benefit of U.S. Provisional Patent Application Ser. No. 60/384,880 filed May 31, 2002, which is herein incorporated by reference in its entirety for all purposes.

BACKGROUND

Genome and transcriptome sequencing profiles can provide important insights into cell physiology, medical diagnosis, prognosis and treatment planning. For example, whole genome single nucleotide polymorphism (SNP) profiling may provide an unbiased method of determining genetic predisposing factors for adverse drug reactions (ADRs). Genetic factors can determine individual susceptibility to both dose-dependent and dose-independent ADRs, see, e.g., Pirmohamed *Trends Pharmacol. Sci.*, 22:298-305 (2001). The cancer phenotype reflects changes in the expression patterns of hundreds or even thousands of genes that occur as a mutation of an oncogene or a tumor suppressor gene. Functional genomic approaches such as DNA microarrays or serial analysis of gene expression (SAGE) can help determine the expression level of genes in a cell or an organism's transcriptome, see, e.g., Polyak, *J. Clin. Oncol.*, 19:2948-2958 (2001). However, understanding the meaning of expression patterns of transcriptomes requires knowledge of the sequences of the messages therein, and up to 30% of mammalian messenger RNA consists of thousands of distinct species, see, e.g., Brenner, *Proc. Natl. Acad. Sci. USA*, 97:1665-1670 (2000). Relatively minor alterations in sequences and expression can have profound impact on cell physiology and organism health.

The majority DNA sequencing methods presently in use are based on the chemical degradation method of Maxam and Gilbert., *Proc. Natl. Acad. Sci. USA*, 74:560-564 (1977) or the dideoxy chain termination approach of Sanger et al., *Proc. Natl. Acad. Sci.*, 74: 5463-5467 (1977). The chain termination method has been improved in several ways and in various forms is widely used in commercial DNA sequencing instruments, e.g. Hunkapiller et al., *Science*, 254: 59-67 (1991).

Both the chemical degradation and chain termination methods require the generation of one or more sets of labeled DNA fragments, each having a common origin and each terminating with a known base. The set or sets of fragments are then separated by size to obtain sequence information. The size separation is usually accomplished by high resolution electrophoresis, either gel or non-gel based, which must have the capacity to distinguish very large fragments differing in size by no more than a single nucleotide. Despite many significant improvements, the technique does not readily lend itself to miniaturization or to massively parallel implementation.

As an alternative to the Sanger-based approaches to DNA sequencing, several so-called "base-by-base" or "single base" sequencing approaches have been explored, see, U.S. Pat. No. 5,302,509; International patent applications WO 91/06678 and WO 93/21340; Canard et al, *Gene*, 148: 1-6 (1994); and Metzker et al., *Nuc. Acids Res.*, 22: 4259-4267 (1994). These approaches are characterized by the determination of a single nucleotide per cycle of chemical or biochemical operations and no requirement of a separation step. Thus, these "single base" approaches allow the possibility of carrying out many thousands of sequencing reactions in parallel, for example, on target polynucleotides attached to microparticles or on solid phase arrays as described, for example in International Patent Application PCT/US95/12678. "Single base" sequencing methods, however, have been hampered by problems such as inefficient chemistries that prevent determination of more than a few nucleotides in a sequencing operation.

Yet another alternative uses make use of the specificity of Watson-Crick base pairing to determine sequence information. In these methods, a polynucleotide is digested with a nuclease to produce a single-stranded region. An oligonucleotide containing a known base is then hybridized to this single stranded-region under stringent hybridization conditions. By repeated cycles of digestion and hybridization, the sequence of the polynucleotide can be determined. Examples, of such methods can be found in U.S. Pat. Nos. 5,552,278; 5,599,675; 5,710,000; 5,714,330; 5,831,065; 6,027,894; 6,013,445; 6,225,077; 6,251,600; 6,258,533; 6,291,181; European Patent Nos. EP 0 927267 and EP 0 703 991; and International Patent Applications WO 98/48047, WO 98/15652 and WO 98/10095. Although, these methods can be adapted for parallel sequencing, for example in arrays, the methods determine only a single nucleotide at a time for each polynucleotide to be sequenced. This slows the sequence determination.

With the need to sequence whole genomes and the increasing reliance on sequence information for diagnostic purposes, what is needed is a method that is capable of simultaneously determining the identity and order of groups of nucleotides on a single polynucleotide and that is suitable for multiplex applications. The present invention meets that need.

SUMMARY

Among the several aspects of the invention is provided a method for determining the sequence of a polynucleotide comprising, providing at least one population of polynucleotides wherein the members of the population share a nucleotide sequence. In addition, at least $4^x$ sets of sequencing adaptors are provided, where each set of sequencing adaptors comprises one of $4^x$ possible combinations of nucleotides in a single-stranded region of x nucleotides long, a nuclease recognition site for a nuclease that produces a single-stranded region of x nucleotides long, but does not cleave within its recognition site, and a detectable optical marker that is unique to that set of sequencing adaptors, where x is an integer equal to 2 or greater, for example, 3 or greater, 4 or greater, 5 or greater, or 6 or greater. Thus, for a given single-stranded region, each set of sequencing adaptors contains a different nucleotide sequence within the single-stranded region, such that all possible nucleotide sequences are represented by the sets of sequencing adaptors. In one embodiment, the sequencing adaptors also comprise a spacer region. In one embodiment, the unique optical marker comprises a microbead. In another embodiment, the microbead is a fluorescent microbead.

In one embodiment, a first end of the polynucleotides to be sequenced are attached to a substrate and a set of initial adaptors comprising a recognition site for a nuclease is ligated to a second end of the polynucleotides contained in the populations to be sequenced. The attachment of the polynucleotides to the substrate can be done before, during or after ligation of the initial adaptors. The nuclease recognition site of the initial adaptors can be the same or different from the nuclease recognition site of the sequencing adaptors. The ligation can be a blunt end ligation or ligation following hybridization of the adaptor to the polynucleotides. In one embodiment, the initial adaptors can further comprise a spacer region.

The polynucleotides to be sequenced are treated with a nuclease specific for the recognition site of the initial adaptors that cleaves the polynucleotides but not the recognition site to produce digested polynucleotides comprising a single-stranded region of at least 2, at least 3, at least 4, at least 5, or 6 at least nucleotides. The digested polynucleotides are then contacted, typically simultaneously, with the $4^x$ sets of sequencing adaptors under conditions such that the sequencing adaptors hybridize to the digested polynucleotides with minimal mismatches to form polynucleotide-adaptor complexes. Polynucleotide-adaptor complexes comprise an adaptor, either a sequencing or an initial adaptor, which is attached to a polynucleotide to be sequenced either by hybridization or hybridization and ligation. In various embodiments, the sequencing adaptors are hybridized to the polynucleotides to be sequenced under moderately stringent, stringent, highly stringent, or very highly stringent conditions. In one embodiment, the hybridized sequencing adaptors are ligated to the polynucleotides to produce adaptor-ligated polynucleotides. In another embodiment, unhybridized sequencing adaptors are removed by washing. In still another embodiment, mismatched adaptors are washed away using conditions such that only perfectly matched adaptors remain hybridized.

The identity of the hybridized sequencing adaptors is determined by their unique optical marker by any means suitable for detection of the marker. Since the identity and order of the nucleotides in the single-stranded region of the sequencing adaptor is known, it is thus possible to simultaneously determining the identity and order of at least 2, at least 3, at least 4, at least 5, or at least 6 nucleotides in the polynucleotides to be sequenced. In one embodiment the detection of the optical marker is made while the sequencing adaptor is attached to the polynucleotide to be sequenced, but the detection can be made after the sequencing adaptor is removed. The polynucleotide-adaptor complexes are treated with a nuclease specific for the recognition site of the hybridized sequencing adaptors, that cleaves the polynucleotides to be sequenced but not the recognition site to produce digested polynucleotides comprising a single-stranded region of at least 2, at least 3, at least 4, at least 5, or at least 6 nucleotides and a sequencing adaptor fragment. The process of hybridizing and ligating sequencing adaptors, optionally removing unligated adaptors, determining the identity of the ligated sequencing adaptors and thus the sequence of the complementary nucleotides on the polynucleotide to be sequenced, and digesting with a nuclease that cuts the polynucleotide but not the recognition site, is repeated at least once. In one embodiment, the process is repeated until the entire polynucleotide has been sequenced, while in other embodiments, a portion of the polynucleotide is sequenced.

The method described herein allows for multiplex determination of sequences. In various embodiments, the method allows for the simultaneous determination of the sequences of at least 10, at least 100, at least 500, at least 1,000, at least 5,000, at least 10,000, at least 100,000 or at least 1,000,000 populations of polynucleotides. In an additional embodiment, polynucleotides that do not hybridize with a sequencing adaptor are blocked or capped to prevent hybridization in a subsequent reaction. In another embodiment, nuclease recognition sites contained in the polynucleotides to be sequenced are blocked. In yet another embodiment, nuclease recognition sites in adaptors that have hybridized to the polynucleotides to be sequenced, but that were not removed by nuclease cleavage are blocked. In one embodiment, nuclease recognition sites are blocked by methylation and a methylation sensitive nuclease is used.

In yet another embodiment, the substrate to which the first end of the polynucleotide to be sequenced is attached, that is the end that does not hybridize to the adaptors, comprises a bead. In one embodiment the substrate is the inner wall of a capillary tube. In an additional embodiment the capillary tube is a double-orificed capillary tube. In still another embodiment, the capillary tubes are part of an array of capillary tubes that may contain at least 10, at least 100, at least 500, at least 1,000, at least 5,000, at least 10,000, at least 100,000 or at least 1,000,000 capillary tubes.

A further aspect provides method for determining the sequence of a polynucleotide comprising, providing at least one population of polynucleotides, preferably a substantially pure population of polynucleotides, wherein members of the population share a nucleotide sequence. Also providing at least $4^x$ sets of sequencing adaptors. The sequencing adaptors contain a single-stranded region x nucleotides long and each set of sequencing adaptors comprises one of $4^x$ possible combinations of nucleotides in a single-stranded region of x nucleotides long, where x is an integer equal to 2, 3, 4, 5, 6 or greater. Each sequencing adaptor also comprises a nuclease recognition site for a nuclease that produces a single-stranded region of x nucleotides long, but does not cleave within the recognition site, where x is an integer equal to 2, 3, 4, 5, 6 or more. Each sequencing adaptor also comprises a fluorescent microsphere marker having a color or emission wavelength that is unique to that set of sequencing adaptors where the markers are selected using the formula:

$$\min_{Cmap}\left(\sum_{\substack{correct \\ adaptors}}\left(\sum_{\substack{incorrect \\ adaptors}} \Delta\hat{G}(\text{adaptor, overhang, } T)\left(Color_{\substack{incorrect \\ adaptor}} \cdot Color_{\substack{correct \\ adaptor}}\right)\right)\right)$$

A first end of the polynucleotides to be sequenced is attached to a substrate and a second end of the polynucleotides to be sequenced is attached to a set of initial adaptors comprising a recognition site for a nuclease that cleaves a polynucleotide to produce a single stranded region, but does not cleave within its recognition site. The polynucleotides are treated with a nuclease specific for the recognition site of the initial adaptors, wherein said nuclease cleaves the polynucleotides but not the recognition site to produce digested polynucleotides comprising a single-stranded region x nucleotides long, with x typically corresponding to the length of the single-stranded region of the sequencing adaptors. Preferably, the polynucleotides do not contain a recognition site for the nuclease or any recognition sites for the nuclease that are within the polynucleotide have been blocked so that only the site contained in the adaptors is recognized. The digested polynucleotides are contacted with the at least $4^x$ sets of sequencing adaptors under conditions, for example stringent conditions, such that the sequencing adaptors hybridize to the digested polynucleotides with minimal mismatches. The hybridized sequencing adaptors are ligated to the polynucleotides to produce adaptor-ligated polynucleotides and the unhybridized sequencing adaptors are removed. The identity of the hybridized sequencing adaptors is determined by their unique markers thus simultaneously determining the identity and order of x nucleotides in said polynucleotides, where x corresponds to the number of nucleotides in the single-stranded region of the sequencing adaptors. The adaptor-ligated polynucleotides are treated with a nuclease specific for the recognition site of the sequencing adaptors, wherein the nuclease cleaves the polynucleotides, but not the recognition site, to produce digested polynucleotides comprising a single-stranded region of x nucleotides and a sequencing adaptor fragment, where x is an integer equal to 2, 3, 4, 5, 6 or greater and the sequencing adaptor fragment removed. The process is then repeated at least once, or until the sequence of the polynucleotide, or portion of interest, has been determined.

Also provided are kits for determining the sequence of a polynucleotide. The kits comprise at least $4^x$ sets of sequencing adaptors, wherein each set of sequencing adaptors comprises one of $4^x$ possible combinations of nucleotides in a single-stranded region of x nucleotides long, a nuclease recognition site for a nuclease that cleaves the polynucleotide to produce a single-stranded region of x nucleotides long but does not cleave the recognition site, and a detectable optical marker that is unique to that set of sequencing adaptors, where x is an integer of 2 or more, 3 or more, 4 or more, 5 or more or 6 or more; and at least one nuclease specific for the sequencing adaptor recognition site. In an additional embodiment, the at least one nuclease is a type IIs restriction enzyme. In one embodiment, the detectable marker comprises a microbead. By unique optical marker, or a detectable optical marker that is unique, is meant that the markers have different properties that can be optically measured directly or indirectly, for example, different sizes, shapes, colors, patterns, or emission of different wavelengths of light. In certain embodiments, the unique optical markers nanocrystal implants in microbeads. In other embodiments, the nanocrystal implants are of different sizes. In one embodiment the nanocrystal implants are cadmium selenide, while in another embodiment the nanocrystal implants are zinc sulfide-capped cadmium selenide. In another embodiment, the microbeads are fluorescent microbeads that can be differentiated on the basis of different fluorescence excitation and/or emission spectra. In a further embodiment, the kit further comprises instructions for sequencing using the methods described herein.

In still another embodiment, the kit further comprises a set of initial adaptors comprising a recognition site for a nuclease wherein said nuclease cleaves the polynucleotides to produce digested polynucleotides comprising a single-stranded region of x nucleotides. In a further embodiment, the initial adaptor recognition site is for a nuclease that cleaves the polynucleotides to be sequenced but not the recognition site. In additional embodiments, the kit further comprises at least one buffer solution used in carrying out the method of the present invention, a ligase, and/or a methylase or methyltransferase.

Another aspect provides a multiplex system for determining the sequence of members of a plurality of populations of polynucleotides comprising, at least $4^x$ sets of sequencing adaptors, wherein each set of sequencing adaptors comprises one of $4^x$ possible combinations of nucleotides in a single-stranded region of x nucleotides long, a nuclease recognition site for a nuclease that cleaves the polynucleotide to produce a single-stranded region of x nucleotides long but does not cleave the recognition site, and a detectable optical marker that is unique to that set of sequencing adaptors, where x is an integer of 2 or more, 3 or more, 4 or more, 5 or more, or 6 or more; a substrate for immobilization of the members of the populations of polynucleotides; and a device for detecting and distinguishing the $4^x$ detectable makers. In one embodiment, the system further comprises at least one nuclease specific for the nuclease recognition site of the adaptors. In an additional embodiment, the nuclease is a type IIs restriction enzyme. In another embodiment, the detectable optical marker comprises a microbead. In certain embodiments, the microbeads comprise nanocrystal implants. In other embodiments, the nanocrystal implants are of different sizes. In one embodiment the nanocrystal implants are cadmium selenide, while in another embodiment the nanocrystal implants are zinc sulfide-capped cadmium selenide. In another embodiment, the microbeads are fluorescent microbeads that can be differentiated on the basis of different fluorescence excitation and/or emission spectra.

In further embodiments, the device for detecting and distinguishing the detectable labels comprises a multicolor imaging device. In a further embodiment, the multicolor imaging device comprises a CCD (charge-coupled device). In yet another embodiment, the multicolor imaging device comprises a fluorescence imager. In another embodiment, the device allows detection of multiple wavelengths and multiple intensities. The system can also comprise a computer comprising a memory storage device which contains executable instructions for, among other things, the introduction and removal of materials used for sequencing in accordance with the methods disclosed herein, sequence data collection, sequence data analysis and/or display of sequence information.

Still another aspect provides a method for diagnosing a genetic susceptibility for a disease, condition, or disorder comprising, obtaining at least one polynucleotide from one or more subjects to be tested; determining the sequence of the polynucleotide by the methods disclosed herein, and comparing to the sequence of the polynucleotide from the subject or subjects to at least one polynucleotide sequence with a known correlation to the disease, condition or disorder of interest.

Yet another aspect provides a method for diagnosing a genetic susceptibility for an adverse drug reaction (ADR) to a drug or combination of drug of interest comprising, obtaining at least one polynucleotide from a subject to be tested; determining the sequence of said polynucleotide by the method of claim 1, and comparing to the sequence of the polynucleotide from said subject to at least one polynucleotide sequence with a known correlation to an adverse drug reaction of interest to the drug or combination of drugs of interest.

BRIEF DESCRIPTION OF THE DRAWINGS

These and other features, aspects, and advantages of the present invention will become better understood with regard to the following description, appended claims and accompanying figures where:

FIG. 1A shows an example of the application of one embodiment of the invention. A polynucleotide to be sequence is attached to a substrate (10) and an initial adaptor (20) attached to the polynucleotide. Although a single sequence is shown attached to the substrate, typically the substrate will contain a plurality of identical polynucleotides. The polynucleotide is digested with a restriction enzyme (RE) that cleaves the polynucleotide, but not the adaptor, at the polynucleotide adaptor border (110) to produce a single-stranded region (120) of 4 nucleotides. A sequencing adaptor with a single-stranded region (30) complementary to the single-stranded region of the polynucleotide (120) is hybridized to the polynucleotide under stringent conditions. The identity of the sequencing adaptor hybridized is determined by means of the unique marker (60) associated with the adaptor. After identification of the hybridized adaptor and thus the complementary nucleotides of the single-stranded region of the polynucleotide to be sequenced, the polynucleotide-adaptor complex is treated with a restriction enzyme (RE) and the process repeated.

FIG. 1B shows an example of a sequencing adaptor comprising a single-stranded region (30) complementary to a single stranded region on the polynucleotide to be sequenced, an optional spacer (40), a recognition site (50) for a restriction enzyme that does not cut within its own recognition site, and a marker (60) that is unique for that adaptor.

DETAILED DESCRIPTION

The following detailed description is provided to aid those skilled in the art in practicing the present invention. Even so, this detailed description should not be construed to unduly limit the present invention as modifications and variations in the embodiments discussed herein can be made by those of ordinary skill in the art without departing from the spirit or scope of the present inventive discovery.

All publications, patents, patent applications, public databases, public database entries, and other references cited in this application are herein incorporated by reference in their entirety as if each individual publication, patent, patent application, public database, public database entry, or other reference was specifically and individually indicated to be incorporated by reference.

As used herein "polynucleotide" and "oligonucleotide" are used interchangeably and refer to a polymeric (2 or more monomers) form of nucleotides of any length, either ribonucleotides or deoxyribonucleotides. The terms refer only to the primary structure of the molecule. Thus, the terms include double- and single-stranded DNA and RNA. The terms also include known types of modifications, for example, labels, methylation, "caps" and/or substitution of one or more of the naturally occurring nucleotides with an analog. Polynucleotides include both sense and antisense strands. Although nucleotides are usually joined by phosphodiester linkages, the terms also include polymeric nucleotides joined by alternative linkages that a susceptible to cleavage, and in particular, enzymatic cleavage.

As used herein, "sequence determination" or "determining the sequence" in reference to a polynucleotide includes the determination of the number, identity and/or order of nucleotides in a polynucleotide or polynucleotides of interest. The determination of partial as well as full-length sequence information for a polynucleotide of interest is included. Although typically sequence information regarding all of the naturally occurring nucleotides, or analogs thereof, is obtained, this is not required. Thus, the determination of a subset of nucleotides is also included, such as the determination of the number and/or order of only purines or of a particular base.

"Properly matched" in reference to the nucleotides of a polynucleotide refers to the situation in a double-stranded segment of a polynucleotide in which the individual nucleotides have undergone correct Watson-Crick base pairing with the nucleotides on the opposite strand, for example A with T and G with C. It should be noted that a base pair can be properly matched even though one or both the members of the pair are nucleotide analogs. "Mismatched" refers to the situation in which one or more nucleotides in a double-stranded polynucleotide have not undergone correct Watson-Crick base pairing such as A with C. Alternatively, when used in the context of the hybridization of an adaptor of the present invention to a polynucleotide, mismatch can refer to the situation in which following hybridization a sequence gap exists between the end of the polynucleotide to be sequenced and the start of the adaptor. As used herein "minimal mismatches" refers to the situation in which less than 10%, less than 5%, less than 2%, less than 1%, less than 0.5%, less than 0.1% or less than 0.01% of the adaptors have undergone incorrect base pairing with the polynucleotide to be sequenced and/or that a gap exists between less than 10%, less than 5%, less than 2%, less than 1%, less than 0.5%, less than 0.1% or less than 0.01% of the adaptors and the polynucleotides to be sequenced following hybridization.

Described herein is a method for determining the complete or partial sequence of a polynucleotide. The method can be applied to any type of polynucleotide, including, without limitation, genomic DNA, cDNA, RNA, mRNA, CRNA, mitochondrial DNA, plastid DNA and the like. The method comprises obtaining one or more populations of polynucleotides wherein the members of each population share a common sequence, that is they are substantially pure populations of a single polynucleotide. As used herein, substantially pure, in the context of polynucleotides, means that the polynucleotide is free from other contaminating proteins, polynucleotides, and other biologicals. Purity may be assayed by standard methods, and will ordinarily be at least about 40% pure, more ordinarily at least about 50% pure, generally at least about 60% pure, more generally at least about 70% pure, often at least about 75% pure, more often at least about 80% pure, typically at least about 85% pure, more typically at least about 90% pure, preferably at least about 95% pure, more preferably at least about 98% pure, more preferably at least 99% pure and still more preferably at least 99.5% pure.

Populations of substantially pure polynucleotides can be obtained by any method known in the art of molecular biology. For example, substantially pure populations can be purified from vectors, such as cloning vectors using procedures found in commonly known references such as Sambrook et al., *Molecular Cloning*, 3rd ed., Cold Spring Harbor Laboratory Press, (2001) and Ausubel et al., *Short Protocols in Molecular Biology*, Wiley and Sons, (1999). Alternatively, substantially pure populations of polynucleotides can be obtained by various polynucleotide amplification methods including, but not limited to, the polymerase chain reaction (PCR) (U.S. Pat. Nos. 4,965,188, 4,800,159, 4,683, 202, and 4,683,195), the ligase chain reaction (LCR) (see, Wu and Wallace, *Genomics*, 4:560-569, (1989); Landegren et al., *Science*, 241:1077-1080, (1988)), transcription amplification (Kwoh et al., *Proc. Natl. Acad. Sci. USA*, 86:1173-1177, (1989)), self-sustained sequence replication (Guatelli et al., *Proc. Natl. Acad. Sci. USA*, 87:1874-1878, (1990)), and nucleic acid based sequence amplification (NASBA).

Populations of polynucleotides can also be the result of chemical synthesis. Methods for the synthesis of polynucleotides are well known in the art and can be found, for example in Beaucage and Iyer, *Tetrahedron*, 48:2223-2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like.

Sequencing is accomplished through the use of double-stranded sequencing adaptors. For a given sequencing reaction, a minimum of $4^x$ different sets of sequencing adaptors are used where x is an integer and is equal to the number of nucleotides present in a single stranded region on an end (overhang) of each set of adaptors. The overhang can be a 3' overhang or a 5' overhang and can be located on either end of the adaptor so long as all adaptors in a given set are the same. In one embodiment, x ranges from 1 to 6, inclusive, in another embodiment from 2 to 6 inclusive, while in still another embodiment, x is from 3 to 6 inclusive. Thus, in the situation when each different set of sequencing adaptors contains a single-stranded overhang of 4 nucleotides, a total of $4^4$ or 256 sets of different sequencing adaptors is used.

In addition to the single stranded region, each sequencing adaptor contains an enzyme recognition site for an enzyme whose cleavage site excludes the recognition site. Such enzymes are often referred to as outside cutters or shift cutters. One group of such enzymes that are useful in the practice of the present method is type IIs restriction enzymes. Type IIs restriction enzymes have a non-palindromic recognition site and cut at a location outside of the recognition site. Type IIs restriction enzymes are well known in the art and are available from a variety of commercial sources. Information on type IIs restriction enzymes is available from a variety of sources including the REBASE restriction enzyme database at http://rebase.neb.com/rebase/. As used herein a "recognition site" refers to a nucleotide sequence that is recognized by a polynucleotide cleaving enzyme, for example a restriction enzyme, that then cuts the polynucleotide at a site fixed with respect to the recognition site. The enzyme recognition site is designed so that when the sequencing adaptor is attached to the polynucleotide to be sequenced, the enzyme will make a cut in the polynucleotide to be sequenced. In one embodiment, the sequencing adaptor is designed so that the enzyme that recognizes the recognition site will cleave within the polynucleotide to be sequenced and at the polynucleotide/adaptor border. In order for this to be accomplished, it may be necessary to include a spacer sequence within the sequencing adaptor. A spacer sequence is simply a set number of nucleotides located within the sequencing adaptor between the recognition site and the cleavage site so that the enzyme cuts the polynucleotide at the desired location. Examples of suitable, naturally-occurring, nucleases include, but are not limited to AarI, AceIII, BbvI, BbvII, Bpu10I, BsmAI, BsmFI, BspMI, Eco31I, Esp3I, FokI, HgaI, Ksp632I, RleAI, SapI, SfaNI, Sth132I, StsI and isoschizomers thereof. Although typically all adaptors will have the same recognition site, this is not necessary so long as the resulting cleavage sites are of the same length and same relative location on the polynucleotide to be sequenced.

As used herein "initial adaptor" refers to the first set of adaptors attached to the polynucleotide to be sequenced. The initial adaptor can be one of the $4^x$ adaptors used for sequencing (sequencing adaptor) or may be an additional adaptor so that the total number of sets of adaptors used for a given sequencing procedure is $4^x+1$. The initial adaptor can be attached to the polynucleotide to be sequenced by hybridization of sticky ends, which may or may not be combined with ligation, or by blunt ligation. Production of sticky ends, that is single-stranded overhangs, can be produced by any means known in the art, for example, but not limited to the use of restriction enzymes or exonucleases. Methods for the production of sticky ends can be found in a variety of references in the art, including, Sambrook et al., *Molecular Cloning*, 3rd ed., Cold Spring Harbor Laboratory Press, (2001) and Ausubel et al., *Short Protocols in Molecular Biology*, Wiley and Sons, (1999). Alternatively, the initial adaptor can be incorporated into the polynucleotide to be sequenced during amplification by using a primer containing the initial adaptor.

If used, ligation can be accomplished either chemically or enzymatically. Methods for chemical ligation are known in the art and can be found for example in Ferris et al., *Nucleosides Nucleotides*, 8:407-414 (1989) and Shabarova et al., *Nuc. Acids Res.*, 19:4247-4251 (1991). In other embodiments, enzymatic ligation is used. General methods for the ligation of polynucleotides can be found in numerous molecular biology references such as those listed herein. Numerous suitable ligases are known in the art, for example, T4 DNA ligase, T7 DNA ligase, *E. coli* DNA ligase, Taq ligase, Pfu ligase and Tth ligase. Generally, ligases require that a 5' phosphate group be present for ligation to the 3' hydroxyl of an abutting strand. This is accomplished by selecting a restriction enzyme that leaves a 5' phosphate. Alternatively this can be accomplished by phosphorylation of the 5' end using a kinase, for example a T4 polynucleotide kinase. In one embodiment, a T4 DNA ligase is used due to its ability to discriminate against single base mismatches at the ligation junction (Alves and Carr, *Nuc. Acids Res.*, 16:8723 (1988), Wu and Wallace, *Gene*, 76:245-254 (1989), Somers et al., *Nuc. Acids Res.*, 22:4840-4841 (1994), and Samiotaki et al., *Genomics*, 20:238-242 (1994)).

The initial adaptor can be attached to either the 3' end or 5' end of the polynucleotide to be sequenced as long as all adaptors are attached to the same end for any given population of polynucleotides to be sequenced. Thus, when multiple populations of polynucleotides are being sequenced, the initial adaptors can be attached to the either the 3' end or 5' end in different populations, but within a given population, all adaptors must be attached at the same end, either all 3' or all 5'. Numerous methods for attachment of initial adaptors to either the 3' or 5' end of the polynucleotides to be sequenced will be apparent to those skilled in the art. For example, when adaptors are attached by hybridization, polynucleotides are provided that have a complementary single-stranded overhang on only one end. In one embodiment, either the 5' ends of all the polynucleotides or the 3' ends of all the polynucleotides in a population are attached to a substrate and thus are unavailable for attachment to an adaptor.

The sequencing adaptors further comprise a detectable optical marker that is unique to each set of sequencing adaptors used. By unique, is meant that it is possible to distinguish the marker for any given adaptor from the markers for all other adaptors in a given set of adaptors. Any system of markers that is capable of producing $4^x$ different makers can be used, where x is an integer equal to the number of nucleotides to be simultaneously identified. For example where 3 nucleotides are simultaneously identified, a minimum of $4^3$ or 64 unique markers is required. In one embodiment, the markers are microbeads, while in a further embodiment, the markers are fluorescent microbeads. In one embodiment, fluorescent markers are selected which have broad excitation, but narrow emission spectra. This allows all of the makers to be excited by a single wavelength while still allowing differentiation between the different markers. Microbeads will generally have a diameter of from about 1 micrometer to about 45 micrometers, for example from about 5 micrometers to about 30 micrometers. In one embodiment, the microbeads have a diameter of about 5 micrometers.

Particular examples of fluorescent microbeads that can be used in the methods disclosed herein include, but are not limited to, the QBEAD™ microsphere system (Quantum Dot Corp., Hayward, Calif.) and the Luminex microsphere system (Luminex Corp., Austin Tex.). For the purposes of this application, microsphere and microbead are used interchangeably. Descriptions of the Quantum Dot Corp microspheres can be found in U.S. Pat. Nos. 5,990,479; 6,207,229 and 6,207,392. Briefly, QBEADS™ comprise microspheres comprising various combinations of coated nanocrystals each of which is capable of light emission at a particular wavelength. The nanocrystals core typically comprise cadmium selenide (CdSe), cadmium telluride (CdTe) or indium arsenide (InAs). The wavelength of the light emitted by the nanocrystals is controlled not only by the core composition, but also by the size of the crystals as well. Thus, 3 nm CdSe nanocrystals emit light at 520 nm, 5.5 nm CdSe nanocrystals emit light at 630 nm, and intermediate sizes emit light at intermediate wavelengths. By combining nanocrystals of varying compositions and/or sizes within a single microsphere, it is possible to produce large numbers of microspheres having unique emission spectra. An example of the use of quantum-dot tagged microbeads can be found in Han et al., *Nature Biotech.*, 19:631-635 (2001).

Luminex microspheres are discussed in U.S. Pat. No. 6,268,222 and PCT publications WO 99/37814 and WO 01/13120. Briefly, the microspheres are microparticles that incorporate polymeric nanoparticles stained with one or more fluorescent dyes. All of the nanoparticles in a given population are dyed with the same concentration of a dye, and by incorporating a known quantity of these nanoparticles into the microsphere, along with known quantities of other nanoparticles stained with different dyes, a multifluorescent microsphere results. By varying the quantity and ratio of different populations of nanoparticles, it is possible to establish and distinguish a large number of discrete populations of microspheres with unique emission spectra. The fluorescent dyes used are of the general class known as cyanine dyes, with emission wavelengths between 550 nm and 900 nm. These dyes may contain methine groups; the number of methine groups influences the spectral properties of the dye. The monomethine dyes that are pyridines typically have a blue to blue-green fluorescence emission, while quinolines have a green to yellow-green fluorescence emission. The trimethine dye analogs are substantially shifted toward red wavelengths, and the pentamethine dyes are shifted even further, often exhibiting infrared fluorescence emission. However, any dye compatible with the composition of the beads can be used.

In another embodiment, the optical markers used comprise submicrometer metallic barcodes. The production and use of submicrometer metallic barcodes is discussed in Nicewarner-Pena et al., *Science*, 294:137-141 (2001). Briefly, these barcodes are cylindrically-shaped metal nanoparticles that can be identified by the pattern of differential optical reflectivity of adjacent stripes. Particles can be manufactured with as many as 13 distinguishable stripes. Reading of the barcodes can be carried out using any suitable method including optical or electron microscopy. Metallic barcodes can be used either alone or in combination with other optical markers such as dyes and in particular fluorescent dyes or fluorophores. For example, nanoparticles comprising N barcode patterns can be combined with 4 fluorophores to produce 4N unique optical markers.

Also provided is a method for marker optimization which provides for a given set of markers associated with specific sequence overhangs a method by which a set of possible color-coded markers, for example fluorescent markers, can be distributed among a set of adaptors having different single-stranded overhangs in such a way that after hybridization of the adaptors on the complementary sequence on the polynucleotide to be sequenced, the color signal from the adaptor with the correct sequence, i.e. a perfect match, is made maximally distinguishable.

To accomplish this, it is first estimated, through thermodynamics, which adaptors will anneal (hybridize) to overhangs on the polynucleotide to be sequenced, and what the level of attraction these adaptors have. It is assumed that the distribution of annealed adaptors is a function of the energy of attraction calculated through thermodynamics. Thus, optical signals are chosen such that incorrectly annealed adaptors have significantly different optical signal (e.g. emission wavelengths) from the correct adaptors and from each other. This has the effect of spreading the background evenly around the color space away from the correct signal.

The free-energy change of annealed nucleotide sequences can be calculated as described in Allawi, *Biochemistry*, 36:10581-10594 (1997); SantaLucia, *Proc. Natl. Acad. Sci. USA*, 95:1460-1465 (1998); and Bommarito, *Nucleic Acid Res.*, 28:1929-1934 (2000). These calculations give the following result: $\Delta G$ (adaptor,overhang,T), which is the free-energy change associated with adaptor (probe) sequence annealing with overhang sequence at temperature T. These free-energy values are calculated for all $N^2$ combinations of adaptors and overhangs where N equals $4^x$. For each overhang, all negative free-energy values represent adaptors that will potentially stick (hybridize) to that overhang. To eliminate the contribution of values corresponding to non-sticking adaptors, the following processing is applied: if $\Delta G$(adaptor, overhang,T)$\geq 0$ then $\Delta \hat{G}$(adaptor, overhang, T)=0, else $\Delta \hat{G}$(adaptor,overhang,T)=$f(\Delta G$(adaptor,overhang,T)) where $f(\Delta G$(adaptor,overhang,T)) is a value that is a function of the free energy. It may be as simple as 1 for all sticking overhangs, or it can be a value that is proportional to the relative affinity of the adaptor for the overhang. In any case, $\Delta \hat{G}$(adaptor,overhang,T) is used as a weighting function to identify which adaptors will hybridize to overhangs, and can additionally weight incorrect (erroneous) adaptors that have high affinity Each probe "color" is in fact a vector with L elements, each associated with a particular wavelength of light, for example fluorescence emission light. Each of these emission wavelengths can be controlled to emit at I different intensity levels. Therefore, the total number of different colors (C) that can be generated is $C=I^L$.

There are further constraints on optical signals that can be imposed to facilitate processing of the total signal emitted. The constraints are as follows:

1. Each unique adaptor has a unique signal vector.
2. All adaptors will have one signal at full intensity to act as a reference for evaluating the overall number of adaptors ligated.
3. All adaptors will have at least one non-zero signal intensity other than the reference
4. Any two non-zero code signals on an adaptor will be separated by at least one intermediate zero intensity signals to reduce cross-talk between signals. The reference signal is not considered in this constraint.

Color vectors can be compared for a measure of similarity by using the dot-product that is defined as:

$$A \cdot B = \{a_1, a_2, \cdots, a_n\} \cdot \{b_1, b_2, \cdots, b_n\} \equiv \sum_{i=1}^{n} a_i b_i$$

Where A & B are color vectors.

The solution to the problem of marker optimization is to minimize the similarity of colors associated with all adaptor sequences that will anneal to a given sequence overhang. Mathematically, that is:

$$\min_{Cmap} \left( \sum_{\substack{correct \\ adaptorss}} \left( \sum_{\substack{incorrrect \\ adaptors}} \Delta \hat{G}(\text{adaptor, overhang}, T) \left( Color_{\substack{anyother \\ adaptor}} \cdot Color_{\substack{correct \\ adaptor}} \right) \right) \right)$$

where Cmap is the set of all color maps between adaptors and colors that satisfy the constraints set out above.

$$\Delta \hat{G}(\text{adaptor, overhang}, T) \left( Color_{\substack{anyother \\ adaptor}} \cdot Color_{\substack{correct \\ adaptor}} \right)$$

will be non-zero whenever an adaptor will anneal with an overhang on a polynucleotide to be sequenced. Summing over all adaptor-overhang combinations except the correct complement (perfect match) will accumulate all of the similarities between colors that can interfere with the detection of a correct match. Although color is used in the present example, it should be recognized that the equations are generally applicable to any optical signal from the marker. Thus, in the equations used herein, the term signal can be substituted for color where signal denotes an optical signal emitted from a marker.

An example is given in Table 1. The algorithm minimizes the sum of all elements of the matrix of Table 1 that are not grayed out. The gray elements (diagonal) are signal values for adapters that indicate the correct sequence. The off-diagonal elements are background values that will confuse the true signal. All zero elements in the matrix are adapters that will not hybridize to the sequence overhang.

TABLE 1

| | | All possible adapters → | | | | | | |
|---|---|---|---|---|---|---|---|---|
| | | $a_1$ | $a_2$ | $a_3$ | $a_4$ | ... | | $a_N$ |
| Correct Adapter ↓ | $a_1$ | 5.1 | 3.1 | 1.1 | 0 | 0 | 0 | ... | 0 |
| | $a_2$ | 2.5 | 4.9 | 2.9 | 2.1 | 0 | 0 | ... | 0 |
| | $a_3$ | 0 | 1.9 | 5.5 | 3.0 | 1.5 | 0.5 | ... | 0 |
| | $a_4$ | 0 | 0.9 | 2.1 | 5.0 | 1.9 | 0 | ... | 0 |
| | ⋮ | 0 | 0 | 0.4 | 3.0 | 5.3 | 2.2 | ... | 0 |
| | | 0 | 0 | 0.1 | 1.1 | 2.4 | 4.8 | ... | 0 |
| | ⋮ | ⋮ | ⋮ | ⋮ | ⋮ | ⋮ | ⋮ | | ⋮ |
| | | 0 | 0.1 | 0.2 | 0 | 0 | 0 | ... | 5.2 |

Either the polynucleotides to be sequenced or the adaptors can optionally be attached to a substrate. In one embodiment, the populations of polynucleotides to be sequenced are attached to a substrate. In the case of polynucleotides to be sequence, all members of a population of polynucleotides are attached by the same end to the substrate. Thus, it does not matter if the polynucleotides are attached by the 3' end or 5' end so long as all members of a population are attached by the same end. In the case of adaptors, the adaptors are attached opposite from the single stranded overhang.

Any substrate known in the art that is suitable for the attachment, either directly or indirectly, of polynucleotides can be used. Non-limiting examples of such substrates include paper, glass (see, e.g., U.S. Pat. No. 5,843,767), ceramics, quartz or other crystalline substrates (e.g. gallium arsenide), metals, metalloids, polacryloylmorpholide, various plastics and plastic copolymers, Nylon™, Teflon™, polyethylene, polypropylene, poly(4-methylbutene), polystyrene, polystyrene/latex, polymethacrylate, poly(ethylene terephthalate), rayon, poly(vinyl butyrate), polyvinylidene difluoride (PVDF) (see, e.g., U.S. Pat. No. 6,024,872), silicones (see, e.g., U.S. Pat. No. 6,096,817), polyformaldehyde (see, e.g., U.S. Pat. Nos. 4,355,153; 4,652,613), cellulose (see, e.g., U.S. Pat. No. 5,068,269), cellulose acetate (see, e.g., U.S. Pat. No. 6,048,457), nitrocellulose, various membranes and gels (e.g., silica aerogels, see, e.g., U.S. Pat. No. 5,795,557), paramagnetic or superparamagnetic microparticles (see, e.g., U.S. Pat. No. 5,939,261) and the like. In one embodiment, the substrate comprises a spatially addressable array. In many embodiments, at least one surface of the array will be substantially flat, although in some embodiments it may be desirable to physically separate regions containing different populations of polynucleotides with, for example, wells, raised regions, pins, etched trenches, or the like.

In one embodiment the substrate is a bead. When beads are used as a substrate in combination with microbeads as markers, the substrate beads should be large enough to allow separation of the substrate beads and the marker beads. Typically the beads will be about 3 times to about 5 times larger than the microbeads. In one embodiment, the beads used as substrates have a diameter of about 45 micrometers or greater. Beads used as a substrate can be made of any material known in the art to which it is possible to attach, either directly or indirectly, polynucleotides. Examples of suitable materials include, without limitation, a polyacrylamide or an equivalent polymer composition; a polymethacylamide, a methyl methacrylate, a glycidyl methacrylate, a dialkylaminoalkyl-(meth)acrylate, or a N,N-dialkylaminoalkyl (meth)acrylate, or an equivalent composition.

The substrate can be a polytetrafluoroethylene filter or a porous filter comprising an equivalent composition. The substrate can comprise an agarose or an equivalent polymer composition; a polyimid or an equivalent polymer composition; a silica or porous glass or an equivalent composition; or, a foam, including porous foam, or an equivalent composition. The foam can comprise a poly(D,L glycolic-co-lactic acid) or a poly(D, L-lactide-co-glycolide) (PLGA) or an equivalent composition. The substrate can also comprise a ceramic or an equivalent composition. The substrate can comprise a poly(ethylene glycol terephthalate) (PEGT) or a poly(butylene terephthalate) (PBT). The substrate can comprise a monodispersed carbon nanotube or a nanotube comprising an equivalent composition. The monodispersed carbon nanotube can comprise a patterned porous silicon or an equivalent composition. The substrate can comprise a polystyrene or an equivalent composition. The polystyrene can comprise a poly(styrene-divinylbenzene) (PS-DVB) or an equivalent composition. The substrate can comprise a plastic or a plastic co-polymer or an equivalent thereof; a polyvinyl, a polypropylene or a polyester or an equivalent thereof; or, a poly(vinyl alcohol) (PVA) hydrogel nanoparticle.

Porous membranes are described, e.g., in Kwon, *J. Biomed. Mater. Res.*, 50:82-89 (2000). Porous foams of macroporous hydrogels are described in Courtney, *J. Biomater. Sci. Polym. Ed.*, 10:1063-1077 (1999). Low density open cell organic foams are described in U.S. Pat. No. 5,945,084. Amorphous poly(D,L) glycolic-co-lactic acids are described in Ranucci, *Tissue Eng.*, 5:407-420 (1999). Porous ceramics are described in Ohgushi, *J. Biomed. Mater. Res.*, 48:913-927 (1999); and, ceramic porous membranes are described in U.S. Pat. Nos. 6,077,800; 5,269,926. Porous sol-gels are described in Juszczak, *J. Biol. Chem.*, 274: 30357-30360 (1999). Porous polytetrafluoroethylene filters are described in Holmquist, *J. Biochem. Biophys. Methods*, 41:49-60 (1999). Porous matrices of poly(ethylene glycol terephthalate) (PEGT) and poly(butylene terephthalate) (PBT) are described in van Dorp, *J. Biomed. Mater. Res.*, 47:292-300 (1999). Monodispersed carbon nanotubes are described in Fan, *Science*, 283:512-514 (1999). Porous glycidyl methacrylate (GMA-GDMA) beads are described in Malmsten, *J. Colloid Interface Sci.*, 220:436-442 (1999). Porous poly(styrene-divinylbenzene) (PS-DVB) particles are described in Leonard, *J. Colloid Interface Sci.*, 220:380-386 (1999). Porous polyacrylonitrile beads are described U.S. Pat. No. 5,047,437. A hydrophilic porous membrane of a non-crystalline hydrophobic polymer and an in situ crosslinked hydrophilic acrylate polymer is described in U.S. Pat. No. 6,083,393. Surface-grafted microporous membranes are described in U.S. Pat. No. 5,547,575. Microporous polyvinylidene fluoride membranes are described in U.S. Pat. No. 5,531,900. Porous membranes comprising cellulose compounds are described in U.S. Pat. No. 5,980,746. A microporous membrane comprising a partially fluorinated polyolefin membrane is described in U.S. Pat. No. 5,209,849. A microfabricated thin-film membrane filter is described in U.S. Pat. No. 5,985,328. Various forms of beads, membrane, particles, nanotubes and microchannel devices and the like, are also described in U.S. Pat. Nos. 5,106,502; 5,022,999; 5,228,994; 5,847,075; 5,871,722; 5,889,073; 5,975,426; 6,007,690; WO 99/19717.

In one alternative embodiment, polynucleotides are attached to the inner surface of capillary tubes. In a further embodiment, the capillary tubes are arranged in arrays. An example of a capillary array that can be used with the present method is the GIGAMATRIX™ system of Diversa Corporation, San Diego, Calif. A description of GIGAMATRIX™ can be found in U.S. Patent Application No. 20020080350A1. The capillary arrays provide a system and method for "retaining" or "holding" polynucleotides to be sequenced. In one embodiment, the polynucleotides can be directly or indirectly "held" or attached to a capillary wall. In one embodiment, the capillary array apparatus includes a plurality of capillaries formed into an array of adjacent capillaries, wherein each capillary comprises at least one wall defining a lumen for "retaining" a sample, for example, a population of polynucleotides to be sequenced. The apparatus can further include interstitial material disposed between adjacent capillaries in the array, and one or more reference indicia formed within of the interstitial material. The capillary can be adapted for being bound in an array of capillaries; e.g., it can include a first wall defining a lumen for retaining the sample and a second wall formed of a filtering material. The filtering material can, e.g., filter excitation energy provided to the lumen to excite the sample.

In one embodiment, the capillary array includes a plurality of individual capillaries comprising at least one outer wall defining a lumen. The outer wall of the capillary can be one or more walls fused together. Similarly, the wall can define a lumen that is cylindrical, square, hexagonal or any other geometric shape so long as the walls form a lumen for retention of a liquid or sample. The capillaries of the capillary array can be held together in close proximity to form a planar structure. The capillaries can be bound together, by being fused (e.g., where the capillaries are made of glass), glued, bonded, or clamped side-by-side. The capillary array can be formed of any number of individual capillaries, for example, a range from 100 to 4,000,000 capillaries. A capillary array can form a microtiter plate having about 100,000 or more individual capillaries bound together.

The capillaries can be formed with an aspect ratio of 50:1. In one embodiment, each capillary has a length of approximately 6 mm, and an internal diameter of the lumen of approximately 200 micrometers. However, other aspect ratios are possible, and range from 10:1 to well over 1000:1. Accordingly, individual capillaries have an inner diameter that ranges from 10-500 micrometers. A capillary having an internal diameter of 200 micrometers and a length of 1 cm has a volume of about 0.3 microliters. The length and width of each capillary can be based on a desired volume and other characteristics, such as evaporation rate, etc. The capillary array can have a density of 500 to more than 10,000 capillaries per $cm^2$. The capillary array can be formed to a width or diameter of about 0.5-20 mm and a height or thickness of 0.05 to about 10 cm. The capillary array can have a thickness of about 0.1 to about 5 cm.

The capillaries can be made according to various manufacturing techniques. In one embodiment, the capillaries are manufactured using a hollow-drawn technique. A cylindrical, or other hollow shape, portion of glass is drawn out to continually longer lengths according to known techniques. The glass is drawn to a desired diameter and then cut into portions of a specific length to form a capillary. Then, a number of individual capillaries are bound together in an array. In an alternative embodiment, a glass etching process is used. A solid tube of glass can be drawn out to a particular width, and cut into portions of a specific length. Then, each solid tube portion is center-etched with acid to form a capillary. The tubes can be bound before or after the etch process. A large number of materials can be suitably used to form a capillary array depending on the manufacturing technique used, including without limitation, glass, metal, semiconductors such as silicon, quartz, ceramics, or various polymers and plastics including, among others, polyethylene, polystyrene, and polypropylene. The internal walls of the capillary array, or portions thereof, may be coated or silanized to modify their surface properties (e.g., to immobilize nucleic acid to be sequenced). For example, the hydrophilicity or hydrophobicity may be altered to promote or reduce wicking or capillary action, respectively. The coating material includes, for example, ligands such as avidin, streptavidin, antibodies, antigens, and other molecules having, for example, specific binding affinity or that can withstand thermal or chemical sterilization.

A capillary array may optionally include reference indicia for providing a positional or alignment reference. The reference indicia may be formed of a pad of glass extending from the surface of the capillary array, or embedded in the interstitial material. In one embodiment, the reference indicia are provided at one or more corners of a microtiter plate formed by the capillary array. A corner of the plate or set of capillaries may be removed, and replaced with the reference indicia. The reference indicia may also be formed at spaced intervals along a capillary array, to provide an indication of a subset of capillaries.

The capillary can include a first wall defining a lumen and a second wall surrounding the first wall. The second wall can thus be made with any material that reduces the "cross-talk" or diffusion of light between adjacent capillaries. Alternatively, the inside surface of the first wall can be coated with a reflective substance to form a mirror, or mirror-like structure, for specular reflection within the lumen. Many different materials can be used in forming the first and second walls, creating different indices of refraction for desired purposes. A filtering material can be formed around the lumen to filter energy to and from the lumen. In one embodiment, the inner wall of the first wall of each capillary of the array, or portion of the array, is coated with the filtering material. In another embodiment, the second wall includes the filtering material. For instance, the second wall can be formed of the filtering material, such as filter glass for example, or in one aspect, the second wall is EMA glass that is doped with an appropriate amount of filtering material. The filtering material can be formed of a color other than black and tuned for a desired excitation/emission filtering characteristic. The filtering material can allow transmission of excitation energy into the lumen, and blocks emission energy from the lumen except through one or more openings at either end of the capillary. When the second wall is formed with a filtering material, certain wavelengths of light representing excitation energy are allowed through to the lumen, and other wavelengths of light representing emission energy are blocked from exiting, except as directed within and along the first wall. The entire capillary array, or a portion thereof, can be tuned to a specific individual wavelength or group of wavelengths, for filtering different bands of light in an excitation and detection process, for example to determine which adaptor has bound to a polynucleotide being sequenced.

In one embodiment, during use, an excitation light is directed into the lumen contacting a particle, for example a fluorescent microbead, and exciting a reporter fluorescent material causing emission of light. The emitted light travels the length of the capillary until it reaches a detector. If the second wall is black EMA glass, emitted light cannot cross contaminate adjacent capillary tubes in a capillary array.

In a detection process using a capillary array, an optical detection system is aligned with the array, which is then scanned for one or more bright spots, representing either a fluorescence or luminescence associated with the hybridization of an adaptor to a polynucleotide to be sequenced. In one embodiment, a capillary array is immersed or contacted with a container containing, for example, sequencing adaptors, wash solutions, solutions with enzymes such as restriction enzymes, exonucleases, ligases, etc. The liquid is wicked into the capillary tubes by capillary action. The natural wicking that occurs as a result of capillary forces obviates the need for pumping equipment and liquid dispensers. Various reagents (e.g., restriction enzymes, exonucleases, ligases) can be introduced simultaneously into the capillaries by placing an open end of the capillaries in the container containing a mixture of the liquid and the reagent(s). Alternatively, the liquid may be wicked a portion of the way into the capillaries, and then the reagent is wicked into a remaining portion of the capillaries.

In order to minimize condensation, a hydrophobic coating can be provided over the outer edge surface of the capillary walls. The coating can reduce the tendency for water or other liquid to accumulate near the outer edge surface of the capillary wall. In one embodiment, the hydrophobic coating is TEFLON™. In one configuration, the coating covers only the outer edge surfaces of the capillary walls. In another configuration, the coating can be formed over both the interstitial material and the outer edge surfaces of the capillary walls. Another advantage of a hydrophobic coating over the outer edge surface of the capillary tubes is during the initial wicking process, some fluidic material in the form of droplets will tend to stick to the surface in which the fluid is introduced. Therefore, the coating minimizes extraneous fluid from forming on the surface of a capillary array, dispensing with a need to shake or knock the extraneous fluid from the surface.

In some embodiments, it is a goal to achieve an initial separation of molecules of interest, e.g., restriction enzymes, exonucleases, ligases. In one embodiment, a bolus of a first component is wicked into a capillary by capillary action until only a portion of the capillary is filled. In one embodiment, pressure is applied at one end of the capillary to prevent the first component from wicking into the entire capillary. The end of the capillary may be completely or partially capped to provide the pressure. An amount of air is then introduced into the capillary adjacent the first component. The air can be introduced by any number of processes. One such process includes moving the first component in one direction within the capillary until a suitable amount of the air is introduced behind the first component. Further movement of the first component by a pulling and/or pushing pressure causes a piston-like action by the first component on the air. The capillary or capillary array is then contacted to a second component. The second component can be pulled into the capillary by the piston-like action created by movement of the first component until a suitable amount of the second component is provided in the capillary, separated from the first component by the air. The capillary or capillary array can then be incubated for a period of time to allow the components to reach an optimal temperature, or for a sufficient time to allow hybridization, for example. The air-bubble separating the two components can be disrupted in order to allow mix the two components together. In one aspect, pressure is applied to either one of the components or to the entire capillary to collapse the bubble.

One of the components may contain paramagnetic beads or particles. The paramagnetic beads can be used to disrupt the air bubble and/or mix the contents of the capillary tube or capillary array. For example, paramagnetic beads can be magnetically attracted from one location in each to another location. The paramagnetic beads are attracted by magnetic fields formed in proximity to the capillary or capillary array. By alternating or adjusting the location of the magnetic field with respect to each capillary, the paramagnetic beads will move within each capillary to mix the liquid within the capillary in which the beads are suspended. This aspect also improves consistency and detectability of the liquid sample among the capillaries.

In another embodiment, a method of forming a multi-component assay includes providing one or more capsules of a second component within a first component. The second component capsules can have an outer layer of a substance that melts or dissolves at a predetermined temperature, thereby releasing the second component into the first component and combining particles among the components. For example, one such substance can be a thermally activated enzyme (e.g., restriction enzymes, exonucleases, ligases). Alternatively, a "release on command" mechanism that is configured to release the second component upon a predetermined event or condition may also be used.

The polynucleotides and/or sequencing adaptors can be attached to the substrate surfaces by any means known in the art, including direct or indirect attachments. The exact method of coupling will vary with the composition of the substrate and the type of linker present, if any. For example, the surfaces can be derivatized for application of the polynucleotide to be sequenced or the adaptor. Reactive functional groups can be, e.g., hydroxyl, carboxyl, amino groups or the like. Silane (e.g., mono- and dihydroxyalkylsilanes, aminoalkyltrialkoxysilanes, 3-aminopropyltriethoxysilane, 3-aminopropyltrimethoxysilane) can provide a hydroxyl functional group for reaction with an amine functional group. In one embodiment, the well known carbodiimide coupling procedure is used.

In one embodiment, the substrate comprises a streptavidin and the polynucleotide or adaptor has been modified to include biotin. The modified polynucleotide or adaptor is thus linked to the surface by a non-covalent interaction of the biotin with the streptavidin. Methods for the biotinylation of polynucleotides are well known to those skilled in the art and include the use of biotinylated primers and ligation of biotinylated linkers or adaptors. In another example, the substrate is polyvinyl, polystyrene, polypropylene or polyester comprising a thin carboxylic acid surface placed on the substrate and the nucleic acid (e.g., oligonucleotide probe, nucleic acid to be sequenced, or a "tethering" nucleic acid) has been modified to include an amine group and the modified nucleic acid is covalently linked to the surface. In another example, the nucleic acid is linked to a glass substrate by an epoxysilane linkage to a terminal amine modification. See, e.g., U.S. Pat. Nos. 6,258,914; 6,309,831; 6,159,695; 6,156,501; 6,150,103; 6,136,962; 6,090,592; 6,048,695; 5,925,552; 5,919,626; 5,837,454; 5,807,756; 5,760,130; 5,736,412; 5,712,171; 5,688,642; 5,466,575; 5,449,767; 5,077,210.

In one embodiment, the polynucleotide or adaptor is attached to the substrate by means of a linker or tether. The polynucleotide or adaptor can be attached to the tether by any of the methods described herein including, but not limited to, ligation, hybridization or a combination of ligation and hybridization. The linker or tether can be attached to the substrate as described herein. Alternatively the linker or tether can be synthesized directly on the substrate using any method known in the art for the synthesis of polynucleotides on solid support, such as those described herein.

After attachment of the initial adaptors to the polynucleotides to be sequenced, the polynucleotide-adaptor complexes are treated with a nuclease under conditions to allow cleavage of the polynucleotides by the nuclease. The exact time of treatment and the exact conditions will vary with such well-known factors such as the nuclease used and the concentration of polynucleotides present. Determination of the optimal times and conditions for nuclease treatment can be determined by the skilled technician without undue experimentation. In one embodiment, the nuclease used is a rare cutter so as to eliminate or minimize the possible of cleaving the polynucleotide to be sequence at a site other than that designated by the adaptor. In another embodiment, prior to treatment of the polynucleotide to be sequenced with a nuclease, all recognition sites for that nuclease contained in the polynucleotide are blocked. Blocking can be achieved in a variety of ways, including methylation and treatment by sequence-specific aptamers, DNA binding proteins, or oligonucleotides that form triplexes. Whenever naturally-occurring nucleases are employed, recognition sites may be blocked by methylating the target polynucleotide with a methylase (methyltransferase) that shares a recognition site with the nuclease being used. That is, for most if not all type IIs restriction nucleases, there exists a so-called "cognate" methylase that methylates the recognition site for the nuclease. For example, the methylase M.FokI shares the same recognition site as the FokI type IIs restriction nuclease. Many such methylases are known in the art and can be found in Roberts et al, *Nuc. Acids Res.*, 31: 418-420 (2003); Nelson et al, *Nuc. Acids Res.*, 21: 3139-3154 (1993), and at the REBASE restriction enzyme database at http://rebase.neb.com/rebase/. Alternatively, if an amplification step such as PCR is employed in preparing polynucleotides for sequencing, methylcytosine triphosphates (e.g., 5-methyldeoxycytosine triphosphate) may be used during amplification so that the natural cytosines are replaced by methylated cytosines in the amplification product. Examples of using methylated dCTPs during polynucleotide amplification to block nuclease cleavage can be found in Han and Rutter, *Nuc. Acids Res.*, 16:11837 (1988) and Padgett and Sorge, *Gene*, 168:31-35 (1996). Blocking of recognition sites can be accomplished prior to or at the same time as addition of the adaptors.

Figure 1:
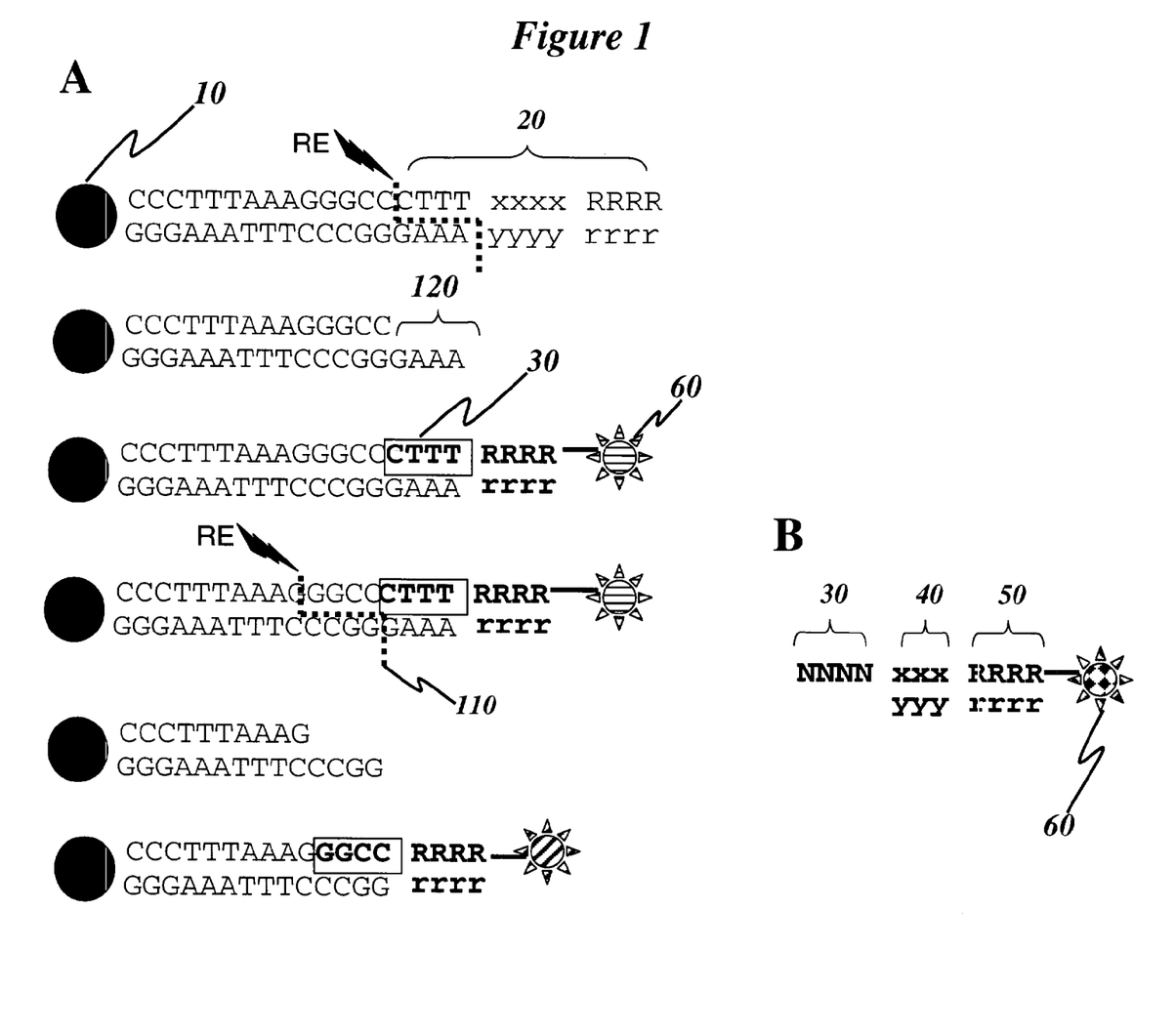
Figure 2:
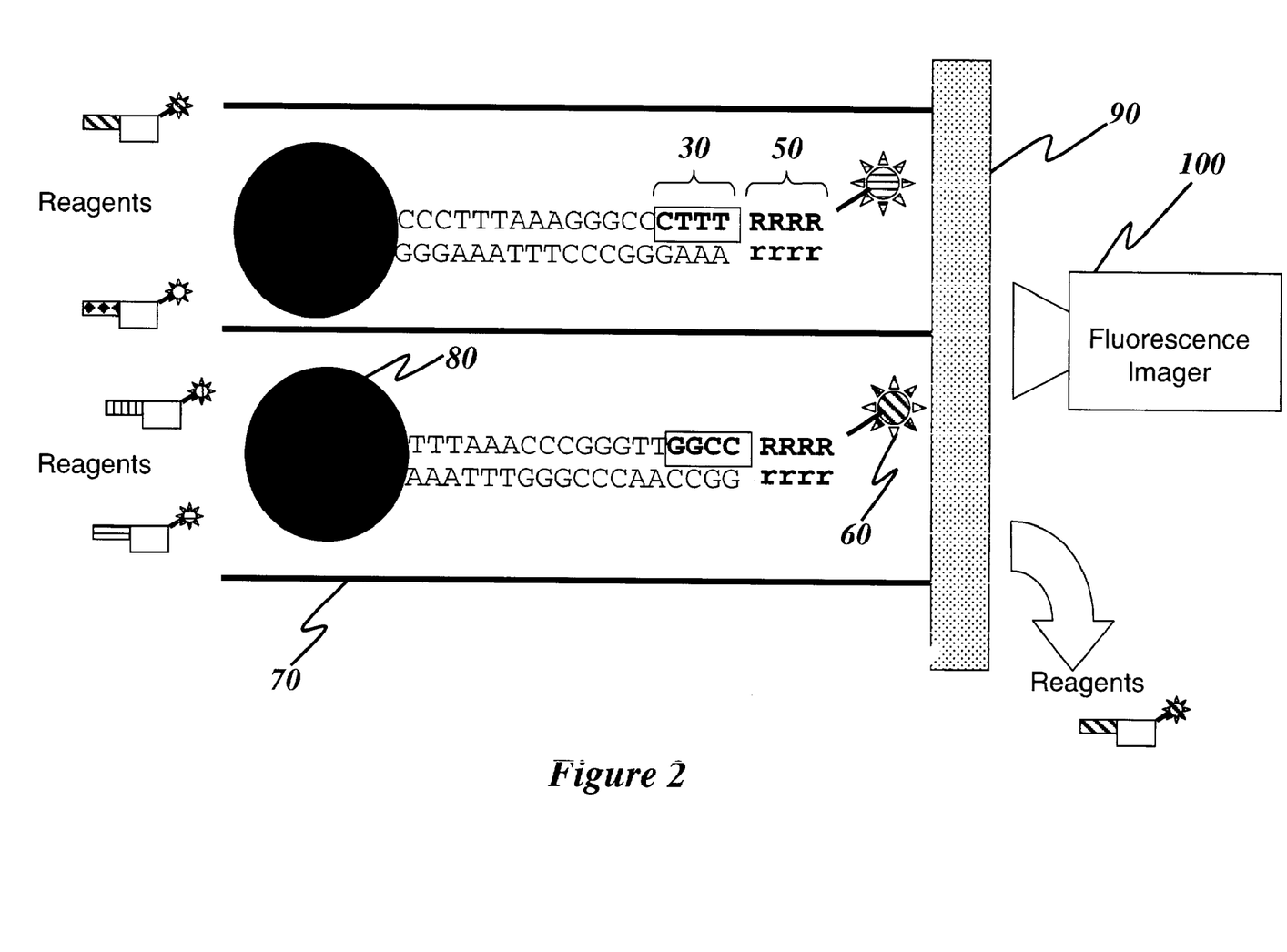
FIG. 2 shows an example of the use of a capillary array in which populations of polynucleotides to be sequenced are attached to beads (80) and the populations are placed into tubes (70) of the array. Although only one polynucleotide is shown attached to a bead, typically a plurality of identical polynucleotides will be attached to a bead. At one end of the tube is a porous membrane or filter (90) that allows adaptors and their unique makers (60) to pass through while retaining the polynucleotides attached to the beads (80). This embodiment also includes a fluorescence imager (100) for identifying the adaptor bound to the polynucleotide.

Treatment of the polynucleotide-adaptor complex with the nuclease cleaves both strands of the double stranded complex to produce an adaptor fragment and a cleaved polynucleotide. The adaptor is designed and the nuclease chosen so that cleavage results in the polynucleotide to be sequenced having a single stranded region of at least 2, for example, 2, 3, 4, 5, 6 or more, nucleotides. FIG. 1A shows a polynucleotide with a single stranded region (120) of 4 nucleotides long. FIG. 1A shows one embodiment, in which one end of the cut is at the polynucleotide/adaptor border (110) such that the single-stranded region contains only nucleotides from the polynucleotide to be sequenced and not from the adaptor. If the resulting single-stranded region contains nucleotides associated with the adaptor, these nucleotides will be constant for each round of sequencing and so are not considered when associating a unique marker with an adaptor. Thus, markers are assigned based only on the composition of the single stranded regions of the adaptors that hybridize with the nucleotides contained in the single stranded region of the polynucleotide to be sequenced following cleavage.

Following treatment with the nuclease, the resulting adaptor fragments can be washed away. Sequencing adaptors are then added under moderately stringent, stringent or highly stringent conditions and allowed to hybridize with the single-stranded regions of the polynucleotides to be sequenced. In one embodiment, hybridization is accomplished under highly stringent conditions such that the number of mismatch or incorrect hybridization reactions are minimized. In another embodiment, hybridization occurs at moderately stringent conditions, followed by washes under stringent and/or highly stringent conditions to remove mismatched adaptors. The number of sequencing adaptors used will vary with the length of the single stranded region of the polynucleotide to be sequence and is given by the formula $4_x$, where x is the number of nucleotides in the single stranded region. This allows for the use of one set of adaptors for each of the possible combinations of nucleotides present in the single-stranded region of the polynucleotide to be sequence For example if the single-stranded region is 3 nucleotides long, then $4^3$ or 64 sets of sequencing adaptors are used, if the single-stranded region is 4 nucleotides long, then $4^4$ or 256 sets of sequencing adaptors are used, and so on.

As is well known in the art, stringency is related to the $T_m$ of the hybrid formed. The $T_m$ (melting temperature) of a nucleic acid hybrid is the temperature at which 50% of the bases are base-paired. For example, if one the partners in a hybrid is a short oligonucleotide of approximately 20 bases, 50% of the duplexes are typically strand separated at the $T_m$. In this case, the $T_m$ reflects a time-independent equilibrium that depends on the concentration of oligonucleotide. As is also well known in the art, $T_m$ is dependent on the composition of the polynucleotide (e.g. length, type of duplex, base composition, and extent of precise base pairing) and the composition of the solvent (e.g. salt concentration and the presence of denaturants such formamide). On equation for the calculation of $T_m$ can be found in Sambrook et al. (*Molecular Cloning*, 2nd ed., Cold Spring Harbor Press, 1989) and is:

$$T_m = 81.5° C. - 16.6(\log_{10}[Na^+]) = 0.41(\%G+C) - 0.63(\% \text{formamide}) - 600/L)$$

Where L is the length of the hybrid in base pairs, the concentration of $Na^+$ is in the range of 0.01M to 0.4M and the G+C content is in the range of 30% to 75%. Alternative equations can be found in Davis et al., *Basic Methods in Molecular Biology*, 2nd ed., Appleton and Lange, 1994, Sec 6-8.

Methods for hybridization and washing are well known in the art and can be found in standard references in molecular biology such as those cited herein. In general, hybridizations are usually carried out in solutions of high ionic strength (6×SSC or 6×SSPE) at a temperature 20-25° C. below the $T_m$. High stringency wash conditions are often determined empirically in preliminary experiments, but usually involve a combination of salt and temperature that is approximately 12-20° C. below the $T_m$. One example of high stringency wash conditions is 1×SSC at 60° C. Another example of high stringency wash conditions is 0.1×SSPE, 0.1% SDS at 42° C. (Meinkoth and Wahl, *Anal. Biochem.*, 138:267-284, 1984). An example of even higher stringency wash conditions is 0.1×SSPE, 0.1% SDS at 50-65° C. In another non-limiting example, high stringency washing is carried out under conditions of 1×SSC and 60° C. As is well recognized in the art, various combinations of factors can result in conditions of substantially equivalent stringency. Such equivalent conditions are within the scope of the present invention.

Following hybridization and, if used, washing to removed mismatched or unhybridized sequencing adaptors, the hybridized sequencing adaptors can be ligated to the polynucleotide. Ligation is useful to discriminate against adaptors that have hybridized to the polynucleotide such that a gap exists between the end of the polynucleotide to be sequenced and the end of the adaptor. Ligation can be accomplished either chemically or enzymatically. In on embodiment, ligation is accomplished enzymatically using a ligase. Any suitable method for ligation known in the art can be used including those detailed herein. Following ligation, removal of unligated adaptors can be accomplished using any known method, for example a high stringency wash.

Following hybridization and, if used, washing, the identity of sequencing adaptors hybridized to the polynucleotides being sequenced is determined using the unique marker associated with each set of adaptors. The exact method of detection used will vary with the type of marker. When a light emitting signal is used, for example a fluorescent marker, any detector capable of measuring differences in wavelength (color) and/or intensity can be used. In addition, detection may also involve light transmission or illumination such as providing an excitation wavelength for a fluorescent marker. Systems for the excitation and detection of fluorescent markers are well known in the art and can be obtained from a variety of sources. Suitable illumination sources include, without limitation, a laser, incandescent bulb, light emitting diode (LED), and arc discharge. Suitable photodetectors include, without limitation, a photodiode array, a charge-coupled device (CCD) (e.g., charge-coupled device), or charge injection device (CID). The systems for practicing the present methods can comprise a charge-coupled device (CCD) for detection/imaging that can also accommodate chemiluminescence, fluorescent and radioisotope target molecule detection, high throughput, and high sensitivity. This detection/imaging apparatus can include imaging arrays (e.g., lensless imaging systems) comprising a plurality of imaging devices, for example, solid state imaging devices, such as an array of CCDs, photoconductor-on-MOS arrays, photoconductor-on-CMOS arrays, charge injection devices (CIDs), photoconductor on thin-film transistor arrays, amorphous silicon sensors, photodiode arrays, or the like. The imaging arrays can be set up in coordination with the capillary array systems of the invention. These devices as corresponding processes of the methods described herein can incorporate in whole or in part designs of detection devices such as described in U.S. Pat. Nos. 6,197,503; 6,197,498; 6,150,147; 6,083,763; 6,066,448; 6,045,996; 6,025,601; 5,599,695; 5,981,956; 5,698,089; 5,578,832; 5,632,957.

In one embodiment, a detection system including a laser source that produces a laser beam is used. The laser beam can be directed into a beam expander configured to produce a wider or less divergent beam for exciting an array such of capillaries. Suitable laser sources include argon or ion lasers. In one embodiment, a cooled CCD can be used.

If light is generated by, for example, excitation of a fluorescent marker, it can be detected by an appropriate light detector or detectors positioned adjacent to an apparatus of the invention. The light detector may be, for example, film, a photomultiplier tube, photodiode, avalanche photo diode, CCD or other light detector or camera. The light detector may be a single detector to detect sequential emissions, such as a scanning laser. Or, the light detector may include a plurality of separate detectors to detect and spatially resolve simultaneous emissions at single or multiple wavelengths of emitted light. The light emitted and detected may be visible light or may be emitted as non-visible radiation such as infrared or ultraviolet radiation. A thermal detector may be used to detect an infrared emission. The detector or detectors may be stationary or movable. The emitted light or other radiation, such as illumination, may be channeled to the detector or detectors by means of lenses, mirrors and fiber optic light guides or light conduits (single, multiple, fixed, or moveable) positioned on or adjacent to at least one surface, such as the surface of an array, for example, a capillary array.

The photodetector can comprise a CCD, CID or an array of photodiode elements. Detection of a position of one or more location in an array having an optical signal can then be determined from the optical input from each element. Alternatively, the array may be scanned by a scanning confocal or phase-contrast fluorescence microscope or the like, where the array is, for example, carried on a movable stage for movement in a X-Y plane as the locations, wells or capillaries in the array are successively aligned with the beam to determine the positions at which an optical signal is detected. A CCD camera or the like can be used in conjunction with the microscope. The detection system can be computer-automated for rapid screening and recovery. A telecentric lens can be used for detection.

In another embodiment, hybridization is detected by using various electromagnetic detection devices, including, for example, optical, magnetic and thermal detection. In yet another embodiment, radioactivity can be detected within a sample (e.g., a capillary tube) using detection methods known in the art. The radiation can be detected at either end of the sample (e.g., capillary tube). Other detection modes include, without limitation, luminescence, fluorescence polarization, time-resolved fluorescence. Luminescence detection includes detecting emitted light that is produced by a chemical or physiological process associated with a sample. Fluorescence polarization detection includes excitation of the contents of the lumen with polarized light. Under such environment, a fluorophore emits polarized light for a particular molecule. However, the emitting molecule can be moving and changing its angle of orientation, and the polarized light emission could become random.

Time-resolved fluorescence includes reading the fluorescence at a predetermined time after excitation. For a long-life fluorophore, the molecule is flashed with excitation energy, which produces emissions from the fluorophore as well as from other particles within the substrate. Emissions from the other particles result in background fluorescence. The background fluorescence normally has a short lifetime relative to the long-life emission from the fluorophore. The emission can be read after excitation is complete, at a time when all background fluorescence usually has short lifetime, and during a time in which the long-life fluorophores continues to fluoresce. Time-resolved fluorescence can be a technique for suppressing background fluorescent activity.

A fluid within a capillary will usually form a meniscus at each end. Any light entering the capillary will be deflected toward the wall, except for paraxial rays, which enter the meniscus curvature at its center. The paraxial rays create a small bright spot in middle of capillary, representing the small amount of light that makes it through. Measurement of the bright spot provides an opportunity to measure how much light is being absorbed on its way through. Thus, one embodiment provides a detection system that includes the use of two different wavelengths. A ratio between a first and a second wavelength indicates how much light is absorbed in the capillary. Alternatively, two images of the capillary can be taken, and a difference between them can be used to ascertain a differential absorbance of a chemical within the capillary. In absorbance detection, only light in the center of the lumen can travel through the capillary. However, if at least one meniscus flattened, the optical efficiency is improved. The meniscus can be kept flat under a number of circumstances, such as in the evaporative wick cycle. The fluid bath can be contained in a clear, light-passing container, and the light source can be directed through the fluid bath into the capillary.

By identification of the signal from the unique marker from the hybridized sequencing adaptor it is possible to determine the identity and sequence of the nucleotides in the polynucleotide that are complementary to the single-stranded region of the sequencing adaptor. For example, if the hybridized adaptor identified has a single-stranded region of 5' atgc, then the polynucleotide is assigned the corresponding sequence 3' tacg. Thus, the present methods allow for the simultaneous determination of the identity and location of nucleotides in a polynucleotide. As will be apparent, the number of nucleotides that can be simultaneously identified is limited only by the number of unique markers available and the length of single-stranded regions produced by the appropriate cleavage enzymes. Thus, for example, simultaneous determination of 2, 3, 4, 5, 6 or more nucleotides is within the scope of the present invention. Although other adaptors which are not perfect matches may hybridize to the polynucleotide to be sequenced, using the methods described herein for marker design and hybridization conditions, the signal from the adaptor that is a perfect match will predominate such that other sequences will be filtered or otherwise eliminated as background.

Following identification of the hybridized sequencing adaptor, the polynucleotide-adaptor complexes are subjected to another nuclease treatment using the recognition site contained in the sequencing adaptor. This results in the formation of another single stranded region on the polynucleotide and a sequencing adaptor fragment. Typically, nuclease cleavage will result in the polynucleotide being shortened by the number of bases that were identified. This will result in each nucleotide in the polynucleotide to be sequenced taking part in adaptor hybridization only once. Positioning of the cleavage site relative to the nuclease recognition site can be accomplished by the use of a spacer in the sequencing adaptor as discussed previously. Alternatively, if desired, the cleavage sites may be positioned such that some nucleotides in the sequence are skipped, or some nucleotides in the sequence are repeated in the next identification step. Also typically, following treatment with the nuclease, the sequencing adaptor fragments produced are removed, for example by washing, in order to decrease background signal. The process of adaptor hybridization, sequence identification, and nuclease cleavage is then repeated until the sequence of all, or the portion of interest, of the polynucleotide is obtained In some cases it may be desirable to block or cap failed sequencing reactions such as is done in polynucleotide or polypeptide synthesis. By "capping" is meant that the polynucleotide is altered so that it is no longer able to participate in the sequencing reaction. Any method that results in the polynucleotide being incapable of participating in subsequent sequencing reactions can be use. For example, polynucleotides that have not hybridized with an adaptor can be block by being made blunt ended. A polynucleotide can be made blunt ended by extending the single stranded region using a polymerase and dNTPs. In one embodiment, the nucleotides used for extension are ddNTPs. Alternatively, the polynucleotides can be made blunt ended by the use of an exonuclease.

In another embodiment, blocking or capping is preformed following the cleavage step. Following addition of the nuclease, some polynucleotide-adaptor complexes may not be cleaved so that the adaptor remains hybridized to the polynucleotide to be sequenced. In this situation, it may be desirable to block the nuclease recognition sites on the uncleaved adaptor to prevent it from participating in the next round of sequencing. Blockage of the recognition site can be achieved by any means known in the art. In one exemplary embodiment, the nuclease recognition site is block by treatment with a methyl transferase as described for blocking recognition sites within the polynucleotide.

One aspect provides a multiplex system for determining the sequence of a plurality of populations of polynucleotide. Such a system comprises $4^x$ sequencing adaptors as described herein. The system further comprises substrate for immobilization of the polynucleotides to be sequenced and a detection system for detecting and distinguishing the $4^x$ unique detectable markers associated with the adaptors. In one embodiment, the substrate is an addressable array. Such arrays can be made of any material known in the art, for example, polymers, plastics, resins, polysaccharides, silica or silica-based materials, carbon, metals, inorganic glasses, membranes, or any of the substrate materials listed herein. In one embodiment, the array comprises wells, for example microtiter plate wells, and the populations of polynucleotides to be sequenced are attached to the walls and/or floor of the microtiter plate wells. In another exemplary embodiment, the array comprises a capillary tube array such as described herein and the populations of polynucleotides to be sequenced are attached to the wall of the capillary tube. In still another embodiment, the array comprises a capillary tube array and the populations of polynucleotides are attached to beads contained within the wells or tubes of the array. In an alternative embodiment, the polynucleotides are attached to magnetic beads and the walls of the array vessels, for example capillary tube walls, are made of a material that attracts the magnetic beads. Alternatively, the walls of the array vessels can be magnetized and the polynucleotides attached to beads that are attracted to the vessel walls. In one embodiment, the capillary tubes are double-orificed capillary tubes. By double-orificed is meant that the capillary tubes have openings at each end, thus allowing the flow of material along the long axis of the tube. One end of these capillary tubes comprises a filtering material. The filtering material contains pores or passages that allow microbeads associated with the sequencing adaptors to pass through the filtering material while retaining the beads to which the polynucleotides to be sequenced are attached. By this method, beads comprising polynucleotides can be subjected to sequentially treatments of sequencing adaptors and other reagents which are then washed out of the tubes and, optionally, recycled for subsequent sequencing reactions.

Fluid containing reagents, enzymes, microbeads and the like used in sequencing can be introduced and removed by any means known in the art. As used herein, the terms liquid reagents or fluid containing reagents encompass liquids that comprise particles such are beads or microbeads. Thus, a fluid or liquid containing polynucleotides attached to beads or sequencing adaptors comprising microbeads would be considered liquid reagents or fluid containing reagents. For example, fluids may be introduced by flooding the surface of the array or submerging the array and removed by simply pouring off the fluid. In another example, liquid reagent exchange is accomplished by wicking. This method in particular adaptable to capillary arrays. In this example, liquid reagents can be introduced in the tube by capillary action or wicking. The first fluid reagent can then be removed and a second liquid reagent introduced by wicking the first liquid out of the first end of the tube while at the same time the second reagent is pulled into second end of the tube. Other methods useful for the introduction of regents into sequencing arrays include, but are not limited to, aspiration, injection, vacuum, and the like. In one embodiment, a flow through system using double-orifice vessels, such as capillary tubes is utilized. In this embodiment liquid reagents are withdrawn from a first end of the vessel and new reagents introduced into the second end of the vessel. Although this system is described as flow through, it should be appreciated that this does not necessary imply constant flow. Thus, the system includes the situation in which after introduction of a fluid into the vessel, the flow is halted to allow sufficient time for a reaction, for example cleavage or hybridization, to occur.

Optionally, fluid removed from the array can be collected in any suitable collection vessel. Examples of suitable collection vessels include, but are not limited to, capillary tubes, microfuge tubes, test tubes, tissue culture tubes, petri dishes, cell culture dishes, microtiter plates, and the like. If desired, regents removed from the array can be recycled during sequencing. For example, sequencing adaptors can be used multiple times during sequencing of a population of polynucleotides.

The system can also comprise a mechanism for the movement of the array relative to detection devices and/or devices for the addition and/or removal of sequencing reagents and materials. This mechanism may comprise a stage containing a means for holding the array and to selectively move the stage and thus the array in 3 dimensions i.e. the x, y and z axis. In one embodiment, movement of the array is achieved by the use of motorized linear actuators. Alternatively, or additional, the system can also comprise one or more mechanisms for moving a detection device and/or devices for the addition and/or removal of sequencing reagents and materials in 2 or 3 dimensions (x, y and z axis) relative to the array using motorized actuators. The system can also comprise a camera for positioning any or all components of the system and a computer processor for controlling the actuators.

The sequencing system also comprises one or more detection devices capable of detecting and distinguishing the markers associated with the sequencing adaptors. Any detection device known in the art and capable of distinguishing between the $4^x$ unique, detectable markers used can be utilized. Examples of suitable detection devices include those described herein including, but not limited to, a photodiode array, a charge-coupled device (CCD) (e.g., charge-coupled device), or charge injection device (CID). The system can also comprise a computer comprising a memory storage device which contains executable instructions for, among other things, the introduction and removal of materials used for sequencing in accordance with the methods disclosed herein, sequence data collection, sequence data analysis and/or display of sequence information.

A further aspect provides a kit for sequencing one or more populations of polynucleotides by the novel methods disclosed herein. Such kits comprises at least $4^x$ sets of sequencing adaptors, where each set of sequencing adaptors comprises one of $4^x$ possible combinations of nucleotides in a single-stranded region of the adaptors x nucleotides long where x is an integer equal to 2, 3, 4, 5, 6 or greater. The kit can comprise greater than $4^x$ adaptors such that some sequences are represented by more than one adaptor. Optionally, the kit can comprise groups of sets of sequencing adaptors, for example, each group containing sets of adaptors for situations when x equal 2, 3, 4, 5, 6, etc. Each of the sequencing adaptors further comprises a recognition site for a nuclease that cleaves a polynucleotide to produce a single-stranded region of x nucleotides long, but does not cleave the recognition site, for example, a type IIs restriction enzyme. The length of the single stranded region produced by the nuclease should correspond to the length of the single-stranded region of the sequencing adaptor. That is, when x is equal to 3 for the sequencing adaptor, a nuclease should be chosen that produces a single-stranded region 3 nucleotides long. The sequencing adaptors also comprise a detectable optical marker that is unique to each set of sequencing adaptors. Any of the suitable markers disclosed herein or equivalent makers known in the art can be used. It should be noted that when multiple groups of sets of sequencing adaptors are provided, the markers can, but need not be, unique between groups. That is, a marker need not be unique between groups, but is unique within a given set of adaptors.

The kit can optionally contain one or more sets of initial adaptors such as those described herein. The initial adaptors may or may not have a single-stranded region. In addition, the initial adaptors need not comprise a unique marker. Typically, the kits will also comprise instructions for carrying out the novel sequencing methods described herein.

The kit can further comprise at least one nuclease that cleaves a polynucleotide to produce a single-stranded region, that is produces a staggered cut or sticky end, but does not cleave the polynucleotide within the recognition site for the enzyme. In one embodiment, the nuclease is a type IIs restriction enzyme. Additionally, the kit can comprise multiple nucleases, for example a variety of type IIs restriction enzymes that produce single-stranded regions of 2, 3, 4, 5, or 6 nucleotides long. Such kits can also comprise additional regents for carrying out the novel sequencing methods described herein. For example, the kits can further comprise one or more buffer solutions, one or more ligases, and various reagents for blocking and capping reactions such as methylases, dNTPs, ddNTPs, polymerases, etc. The kits may also comprise vessels and arrays for conducting the sequencing reactions, for example capillary arrays.

The method further provides a method for diagnosinig a genetic susceptibility for a disease, condition, or disorder of interest. As used in the context of diagnosis, the terms "genetic predisposition", "genetic susceptibility" and "susceptibility" all refer to the likelihood that an individual subject will develop a particular disease, condition or disorder. For example, a subject with an increased susceptibility or predisposition will be more likely than average to develop a disease, while a subject with a decreased susceptibility will be less likely than average to develop the disease. In this aspect, a biological sample is obtained from at least one test subject. The subject can be a human being or any vertebrate animal. The biological sample must contain polynucleotides, for example, DNA. Samples that do not contain DNA, for example, pure samples of mammalian red blood cells, are not suitable for use in the method. The polynucleotide, or a portion thereof, is then sequenced using the method described herein. The sequence obtained is then compared to at least one reference sequence with a known correlation to the disease, condition or disorder of interest. Alternatively, a biological sample can be obtained from at least one reference subject known to have or be susceptible to the disease, condition or disorder of interest, sequencing the biological sample from the reference subject, and comparing the sequence from the reference subject to the sequence obtained from the test subject.

The method further provides a method for diagnosing a genetic susceptibility for adverse drug reactions. As used in this context the terms "genetic predisposition", "genetic susceptibility" and "susceptibility" all refer to the likelihood that an individual subject will develop a particular adverse drug reaction For example, a subject with an increased susceptibility or predisposition will be more likely than average to exhibit an adverse drug reaction, while a subject with a decreased susceptibility will be less likely than average to develop an adverse reaction. In this aspect, a biological sample is obtained from at least one test subject. The subject can be a human being or any vertebrate animal. The biological sample must contain polynucleotides, for example, DNA. Samples that do not contain DNA, for example, pure samples of mammalian red blood cells, are not suitable for use in the method. The polynucleotide, or a portion thereof, is then sequenced using the method described herein. The sequence obtained is then compared to at least one reference sequence with a known correlation to development of an adverse reaction to a particular drug or combination of drugs. Alternatively, a biological sample can be obtained from at least one reference subject known to have or be susceptible to adverse reactions to the drug or drugs of interest, sequencing the biological sample from the reference subject, and comparing the sequence from the reference subject to the sequence obtained from the test subject.

CONCLUSION

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventor does not intend to be bound by those conclusions and functions, but puts them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A method for determining the sequence of a polynucleotide comprising,
   a) providing at least one population of polynucleotides wherein members of the population share a nucleotide sequence;
   b) providing $4^x$ sets of sequencing adaptors, wherein each set of sequencing adaptors comprises one of $4^x$ possible combinations of nucleotides in a single-stranded region of x nucleotides long, a nuclease recognition site for a nuclease that produces a single-stranded region of x nucleotides long, and a detectable optical marker that is unique to that set of sequencing adaptors, where x is an integer of 3 or more;

c) attaching a first end of said polynucleotides to a substrate and ligating to a second end of said polynucleotides a set of initial adaptors comprising a recognition site for a nuclease;

d) treating said polynucleotides with a nuclease specific for the recognition site of the initial adaptors, wherein said nuclease cleaves the polynucleotides but not the recognition site to produce digested polynucleotides comprising a single-stranded region of x nucleotides;

e) simultaneously contacting the digested polynucleotides with the $4^x$ sets of sequencing adaptors under conditions such that the sequencing adaptors hybridize to the digested polynucleotides with minimal mismatches;

f) ligating the hybridized sequencing adaptors to the polynucleotides to produce adaptor-ligated polynucleotides;

g) removing unhybridized sequencing adaptors;

h) determining the identity of the hybridized sequencing adaptors by their unique marker thus simultaneously determining the identity and order of x nucleotides in said polynucleotides;

i) treating the adaptor-ligated polynucleotides with a nuclease specific for the recognition site of the sequencing adaptors, wherein said nuclease cleaves the polynucleotides but not the recognition site to produce digested polynucleotides comprising a single-stranded region of x nucleotides and a sequencing adaptor fragment; and j) repeating e) through i) at least once, or until the sequence of the polynucleotide has been determined wherein said optical markers are selected using the formula:

$$\min_{Cmap} \left( \sum_{\substack{correct \\ adaptorss}} \left( \sum_{\substack{incorrrect \\ adaptors}} \Delta \hat{G}(\text{adaptor, overhang, } T) \left( Color_{\substack{anyother \\ adaptor}} \cdot Color_{\substack{correct \\ adaptor}} \right) \right) \right).$$

2. A method for determining the sequence of a polynucleotide comprising, a) providing at least one population of polynucleotides wherein members of the population share a nucleotide sequence;

b) providing $4^x$ sets of sequencing adaptors, wherein each set of sequencing adaptors comprises one of $4^x$ possible combinations of nucleotides in a single-stranded region of x nucleotides long, a nuclease recognition site for a type IIs restriction enzyme that produces a single-stranded region of x nucleotides long, and a fluorescent microsphere with an emission spectrum that is unique to that set of sequencing adaptors, where x is an integer of 3 or more and wherein said microspheres are selected using the formula:

$$\min_{Cmap} \left( \sum_{\substack{correct \\ adaptorss}} \left( \sum_{\substack{incorrrect \\ adaptors}} \Delta \hat{G}(\text{adaptor, overhang, } T) \left( Color_{\substack{anyother \\ adaptor}} \cdot Color_{\substack{correct \\ adaptor}} \right) \right) \right);$$

c) attaching a first end of said polynucleotides to a substrate and ligating to a second end of said polynucleotides a set of initial adaptors comprising a recognition site for a type IIs restriction enzyme;

d) treating said polynucleotides with a type IIs restriction enzyme specific for the recognition site of the initial adaptors to produce digested polynucleotides comprising a single-stranded region of x nucleotides where x is equal to the number of nucleotides in the single-stranded region of the sequencing adaptors;

e) simultaneously contacting the digested polynucleotides with the $4^x$ sets of sequencing adaptors under stringent conditions such that the sequencing adaptors hybridize to the digested polynucleotides with minimal mismatches;

f) ligating the hybridized sequencing adaptors to the polynucleotides to produce adaptor-ligated polynucleotides;

g) removing unhybridized sequencing adaptors;

h) determining the identity of the sequencing adaptors while hybridized to the polynucleotide to be sequenced by their fluorescent microsphere, thus simultaneously determining the identity and order of x nucleotides in said polynucleotides;

i) treating the adaptor-ligated polynucleotides with a type IIs restriction enzyme specific for the recognition site of the sequencing adaptors to produce digested polynucleotides comprising a single-stranded region of x nucleotides and a sequencing adaptor fragment;

j) removing the sequencing fragment; and k) repeating e) through j) at least once, or until the sequence of the polynucleotide has been determined.

* * * * *